(12) United States Patent
Berner et al.

(10) Patent No.: US 9,980,903 B2
(45) Date of Patent: May 29, 2018

(54) GASTRIC RETENTIVE ORAL DOSAGE FORM WITH RESTRICTED DRUG RELEASE IN THE LOWER GASTROINTESTINAL TRACT

(75) Inventors: Bret Berner, Half Moon Bay, CA (US); Jenny Louie-Helm, Fremont, CA (US); John W. Shell, Hillsborough, CA (US); Barbara Shell, legal representative, Hillsborough, CA (US)

(73) Assignee: Depomed, Inc., Newark, CA (US)

( * ) Notice: Subject to any disclaimer, the term of this patent is extended or adjusted under 35 U.S.C. 154(b) by 0 days. days.

(21) Appl. No.: 13/153,211

(22) Filed: Jun. 3, 2011

(65) Prior Publication Data

US 2011/0301129 A1    Dec. 8, 2011

Related U.S. Application Data

(60) Division of application No. 10/769,574, filed on Jan. 29, 2004, now Pat. No. 7,976,870, which is a division of application No. 10/024,932, filed on Dec. 18, 2001, now abandoned, which is a continuation-in-part of application No. 10/045,816, filed on Oct. 25, 2001, now abandoned.

(51) Int. Cl.
| | |
|---|---|
| *A61K 9/20* | (2006.01) |
| *A61K 31/197* | (2006.01) |
| *A61K 9/00* | (2006.01) |
| *A61K 31/00* | (2006.01) |
| *A61K 31/65* | (2006.01) |
| *A61K 31/195* | (2006.01) |
| *A61K 31/496* | (2006.01) |

(52) U.S. Cl.
CPC ............. *A61K 9/0065* (2013.01); *A61K 9/20* (2013.01); *A61K 31/00* (2013.01); *A61K 31/195* (2013.01); *A61K 31/197* (2013.01); *A61K 31/496* (2013.01); *A61K 31/65* (2013.01); *A61K 9/2031* (2013.01)

(58) Field of Classification Search
CPC ...... A61K 9/0065; A61K 31/65; A61K 31/00; A61K 9/2031; A61K 31/197; A61K 9/20; A61K 31/195; A61K 31/496
USPC ........................................................ 424/468
See application file for complete search history.

(56) References Cited

U.S. PATENT DOCUMENTS

| | | |
|---|---|---|
| 4,434,153 A | 2/1984 | Urquhart et al. |
| 4,670,444 A | 6/1987 | Grohe et al. |
| 4,690,824 A | 9/1987 | Powell et al. |
| 4,695,467 A | 9/1987 | Uemura et al. |
| 4,748,023 A | 5/1988 | Tamas et al. |
| 4,753,801 A | 6/1988 | Oren et al. |
| 4,786,503 A | 11/1988 | Edgren et al. |
| 4,839,177 A | 6/1989 | Colombo et al. |
| 4,851,232 A | 7/1989 | Urquhart et al. |
| 4,865,849 A | 9/1989 | Conte et al. |
| 4,871,548 A | 10/1989 | Edgren et al. |
| 4,910,021 A | 3/1990 | Davis et al. |
| 5,002,772 A | 3/1991 | Curatolo et al. |
| 5,007,790 A | 4/1991 | Shell |
| 5,064,656 A | 11/1991 | Gergely et al. |
| 5,085,865 A | 2/1992 | Nayak |
| 5,213,808 A | 5/1993 | Bar-Shalom et al. |
| 5,232,704 A | 8/1993 | Franz et al. |
| 5,382,435 A | 1/1995 | Geary et al. |
| 5,393,765 A | 2/1995 | Infeld et al. |
| 5,422,123 A | 6/1995 | Conte et al. |
| 5,425,950 A | 6/1995 | Dandiker et al. |
| 5,458,887 A | 10/1995 | Chen et al. |
| 5,458,888 A | 10/1995 | Chen |
| 5,472,708 A | 12/1995 | Chen |
| 5,487,901 A | 1/1996 | Conte et al. |
| 5,508,040 A | 4/1996 | Chen |
| 5,549,913 A | 8/1996 | Colombo et al. |
| 5,582,837 A | 10/1996 | Shell |
| 5,609,590 A | 3/1997 | Herbig et al. |
| 5,626,874 A | 5/1997 | Conte et al. |

(Continued)

FOREIGN PATENT DOCUMENTS

| | | |
|---|---|---|
| CA | 2143500 A1 | 8/1995 |
| EP | 0598309 B1 | 5/1994 |

(Continued)

OTHER PUBLICATIONS

US 5,464,663, 11/1995, Conte et al. (withdrawn)
Magnesium Stearate Data Sheet. Datasheet [online]. TOXNET, National Library of Medicine GSDB Database, 2005, [retrieved on Jun. 22, 2015]. Retrieved from the Internet<URL:http://toxnet.nlm.nih.gov/cgi-bin/sis/search/a?dbs+hsdb:@term+@DOCNO+713>, 3 pages.*
U.S. Appl. No. 09/425,491, filed Oct. 22, 1999, Shell et al.
Abrahamsson et al., "Absorption, Gastrointestinal Transit, and Tablet Erosion of Felodipine Extended-Release (ER) Tablets," Pharmaceutical Research Nol. 10, No. 5, pp. 709-714 (1993).
Apicella et al., "Poly(ethylene oxide) (PEO) and Different Molecular Weight PEO Blends Monolithic Devices for Drug Release," Biomaterials vol. 14, No. 2. pp. 83-90 (1993).

(Continued)

*Primary Examiner* — John Pak
*Assistant Examiner* — Andriae M Holt
(74) *Attorney, Agent, or Firm* — McDermott Will & Emery LLP

(57) ABSTRACT

Controlled release oral dosage forms are provided for the continuous, sustained administration of a pharmacologically active agent to the upper gastrointestinal tract of a patient in whom the fed mode as been induced. The majority of the agent is delivered, on an extended release basis, to the stomach, duodenum and upper regions of the small intestine, with drug delivery in the lower gastrointestinal tract and colon substantially restricted. The dosage form comprises a matrix of a biocompatible, hydrophilic, erodible polymer with an active agent incorporated therein, wherein the polymer is one that both swells in the presence of water and gradually erodes over a time period of hours, with swelling and erosion commencing upon contact with gastric fluid, and drug release rate primarily controlled by erosion rate.

13 Claims, 9 Drawing Sheets

(56) References Cited

U.S. PATENT DOCUMENTS

| | | | |
|---|---|---|---|
| 5,650,169 A | 7/1997 | Conte et al. | |
| 5,651,985 A | 7/1997 | Penners et al. | |
| 5,681,583 A | 10/1997 | Conte et al. | |
| 5,688,776 A | 11/1997 | Baur et al. | |
| 5,736,159 A | 4/1998 | Chen et al. | |
| 5,738,874 A | 4/1998 | Conte et al. | |
| 5,780,057 A | 7/1998 | Conte et al. | |
| 5,783,212 A | 7/1998 | Fassihi et al. | |
| 5,811,126 A | 9/1998 | Krishnamurthy | |
| 5,837,379 A | 11/1998 | Chen et al. | |
| 5,840,329 A | 11/1998 | Bai | |
| 5,840,332 A | 11/1998 | Lerner et al. | |
| 5,861,173 A | 1/1999 | Nishioka et al. | |
| 5,891,474 A | 4/1999 | Busetti et al. | |
| 5,897,874 A | 4/1999 | Stevens et al. | |
| 5,916,595 A | 6/1999 | Chen et al. | |
| 5,945,125 A | 8/1999 | Kim | |
| 5,972,389 A | 10/1999 | Shell et al. | |
| 6,027,748 A | 2/2000 | Conte et al. | |
| 6,033,385 A | 3/2000 | Qiu et al. | |
| 6,048,547 A | 4/2000 | Seth et al. | |
| 6,093,420 A | 7/2000 | Baichwal | |
| 6,120,803 A | 9/2000 | Wong et al. | |
| 6,207,197 B1 | 3/2001 | Illum et al. | |
| 6,221,395 B1 | 4/2001 | Maggi et al. | |
| 6,248,363 B1 | 6/2001 | Patel et al. | |
| 6,261,601 B1 | 7/2001 | Talwar et al. | |
| 6,340,475 B2 | 1/2002 | Shell et al. | |
| 6,368,628 B1 | 4/2002 | Seth | |
| 6,451,808 B1 | 9/2002 | Cowles | |
| 6,488,962 B1 | 12/2002 | Berner et al. | |
| 6,562,375 B1 | 5/2003 | Sako et al. | |
| 6,635,280 B2 | 10/2003 | Shell et al. | |
| 6,682,759 B2 | 1/2004 | Lim et al. | |
| 6,696,085 B2 * | 2/2004 | Rault | A61K 9/2027 424/464 |
| 2001/0018070 A1 | 8/2001 | Shell et al. | |
| 2003/0031711 A1 | 2/2003 | Fara et al. | |
| 2003/0039688 A1 | 2/2003 | Shell et al. | |
| 2003/0056896 A1* | 3/2003 | Jao et al. | 156/327 |
| 2003/0091630 A1 | 5/2003 | Louie-Helm et al. | |
| 2003/0133985 A1 | 7/2003 | Louie-Helm et al. | |
| 2003/0147952 A1 | 8/2003 | Lim et al. | |
| 2003/0152622 A1 | 8/2003 | Louie-Helm et al. | |
| 2004/0156899 A1 | 8/2004 | Louie-Helm et al. | |

FOREIGN PATENT DOCUMENTS

| | | |
|---|---|---|
| EP | 0795324 A2 | 9/1997 |
| GB | 1330829 A | 9/1973 |
| WO | WO 1996/026717 A1 | 9/1996 |
| WO | WO 1996/032097 A1 | 10/1996 |
| WO | WO 1998/055107 A1 | 12/1998 |
| WO | WO 2000/023045 A1 | 4/2000 |
| WO | WO 2000/038650 A1 | 7/2000 |
| WO | WO 2001/032217 A3 | 5/2001 |
| WO | WO 2001/056544 A3 | 8/2001 |
| WO | WO 2001/097783 A1 | 12/2001 |
| WO | WO 2002/083687 A1 | 10/2002 |

OTHER PUBLICATIONS

Bloem et al., "A controlled trial of a slow-release form of furosemide in hypertension," Curr. Ther. Res., vol. 29, pp. 577-583 (1981).

Boles Ponto et al., "Furosemide (frusemide): a pharmacokineticl pharmacodynamic review," Clin. Pharmacokinetics, vol. 18, pp. 381-471 (1990).

CIPRO (ciprofioxacin hydrochloride) Tablets, CIPRO (ciprofioxacin) 5% and 10% Oral Suspension Drug Information Sheet, Aug. 20, 2000, pp. 1-9.

Ciprofioxicin, Datasheet [online], MedSafe Information for Health Professionals, 2008 [retrieved on Jan. 14, 2010], Retrieved from the Internet: <URL:http://www.medsafe.govt.nz/ProfsiDatasheetic/Ciproxinhocotic,htrn>, pp. 1-10.

Ciprofloxacin Patient Information Sheet, Patient Information Sheet. [online]. Preferred Pharmaceuticals, 2000 [retrieved on Jul. 30, 2010]. Retrieved from the Internet: <URL: http://www.preferredpharmaceuticals.comIPEIICiprofloxacin.pdf.

Columbo et al., "Drug Release Modulation by Physical Restrictions of Matrix Swelling," International Journal of Pharmaceutics, vol. 63, pp. 43-48 (1990).

Conte et al., "Modulation of the Dissolution Profiles from Geomatrix® Multi-Layer Matrix Tablets Containing Drugs of Different Solubility," Biomaterials vol. 17, No. 9, 889-896 (1996).

Davis et al., "The Effect of Density on the Gastric Emptying of Single- and Multiple-Unit Dosage Forms," Pharmaceutical Research vol. 3, No. 4, pp. 208-213 (1986).

Deshpande et al., "Development of a Novel Controlled-Release System for Gastric Retention," Pharmaceutical Research, vol. 14, No. 6, pp. 815-819 (1997).

Dow Chemical U.S.A. Product Information Publication, "Formulating for Controlled Release with METHOCEL Cellulose Ethers", Oct. 5, 2007. 34 pages.

Gabr et al., "Formulation and evaluation of buffered floating furosemide delivery systems," S.T.P. Pharma Sci., vol. 10, pp. 181-186 (2000).

Gusler et al., "Pharmacokinetics of Metformin Gastric-Retentive Tablets in Healthy Volunteers," The Journal of Clinical Pharmacology, vol. 41, No. 6, pp. 655-661 (2001).

Hou et al., "Gastric Retentive Dosage Forms: A Review," Crit. Rev. Ther. Drug Carrier Syst., vol. 20, No. 6, pp. 461-497 (2003).

Huber et al., "Utilization of Hydrophilic Gums for the Control of Drug Release from Tablet Formulations. I. Disintegration and Dissolution Behavior," Journal of Pharmaceutical Sciences, vol. 55, No. 9, pp. 974-976 (1966).

Hwang et al., "Gastric Retentive Drug-Delivery Systems," Critical Reviews in Therapeutic Drug Carrier Systems, vol. 15, No. 3, pp. 243-284 (1998).

Iannuccelli et al., "PVP solid dispersions for the controlled release of furosemide from a floating multiple-dose unit system," Drug Dev. Indus. Pharm., vol. 26, No. 595-603 (2000).

Kaniwa et al., "The bioavailability of flufenamic acid and its dissolution rate from capsules," Intl. J. Clin. Pharmacol. Ther. Toxicol., vol. 21, pp. 56-63 (1983).

Katori et al., "Estimation of Agitation Intensity in the GI Tract in Humans and Dogs Based on in Vitro/in Vivo Correlation," Pharmaceutical Research, vol. 12, No. 2, pp. 237-243 (1995).

Kim, "Drug Release from Compressed Hydrophilic POLYOX-WSR Tablets," Journal of Pharmaceutical Sciences, vol. 84, No. 3, pp. 303-306 (1995).

Korsmeyer et al., "Mechanisms of Solute Release from Porous Hydrophilic Polymers," International Journal of Pharmaceutics vol. 15, pp. 25-35 (1983).

Lapidus et al., "Some Factors Affecting the Release of a Water-Soluble Drug from a Compressed Hydrophilic Matrix," Journal of Pharmaceutical Sciences vol. 55, No. 8, pp. 840-843 (1966).

Louie-Helm et al., "Pharmacokinetics of Ciprofloxacin Gastric Retentive Tablets in Healthy Volunteers," Control Release Soc. 28th An. Meeting Proc., No. 6044 (2001).

Maggi et al., "Highly Swellable, Multi-Layer Tablets to Prolong the Residence Time of the Delivery Device in the Stomach," Abstracts /Journal of Controlled Release, vol. 64, pp. 333-334 (2000).

Maggi et al., "High Molecular Weight Polyethylene Oxides (PEOs) as an Alternative to HPMC in Controlled Release Dosage Forms," International Journal of Pharmaceutics, vol. 195, pp. 229-238 (2000).

Menon et al., "Development and evaluation of a monolithic floating dosage form for furosemide," J. Pharmac. Sci., vol. 83, pp. 239-245 (1994).

Prostatitis, Datasheet [online], WebMD, 2005 [retrieved on Jan. 14, 2010], Retrieved from the Internet: <URL:http://men,wehmd,comiprostatitis>, pp. 1-4.

Rao et al., "Swelling Controlled-Release Systems: Recent Developments and Applications," International Journal of Pharmaceutics, vol. 48, pp. 1-13 (1988).

(56) References Cited

OTHER PUBLICATIONS

Reynolds et al., "Polymer Erosion and Drug Release Characterization of Hydroxypropyl Methylcellulose Matrices," Journal of Pharmaceutical Sciences, vol. 87, No. 9, pp. 1115-1123 (1998).

Shameem et al., "Oral Solid Controlled Release Dosage Forms: Role of GI-Mechanical Destructive Forces and Colonic Release in Drug Absorption Under Fasted and Fed Conditions in Humans," Pharmaceutical Research, vol. 12, No. 7, pp. 1049-1054 (1995).

Siepmann et al., "A New Model Describing the Swelling and Drug Release Kinetics from Hydroxypropyl Methylcellulose Tablets," Journal of Pharmaceutical Sciences, vol. 88, No. 1, pp. 65-72 (1999).

Siepmann et al., "HPMC Matrices for Controlled Drug Delivery: A New Model Combining Diffusion, Swelling, and Dissolution Mechanisms and Predicting the Release of Kinetics," Pharmaceutical Research vol. 16, No. 11, pp. 1748-1756 (1999).

Uchino et al., "clinical pharmacokinetics and diuretic effect of furosemide in plain tablet and retard capsule with normal subjects and cirrhotic patients," J. Pharm. Dyn., vol. 6, pp. 684-691 (1983).

Wakelkamp et al., "The influence of frusemide formulation on diuretic effect and efficiency," J. Clin. Pharmacol., vol. 48, pp. 361-366 (1999).

Yang et al., "Zero-Order Release Kinetics from a Self-Correcting Floatable Asymmetric Configuration Drug Delivery System," Journal of Pharmaceutical Sciences, vol. 85, No. 2, pp. 170-173 (1996).

Alprazolam FAQ v3.2 [online]. Erowid Alprazolam Vault, 2011 [retrieved on Sep. 28, 2015]. Retrieved from the Internet:<URL:https://www.erowid.org/pharms/alprazolam_faq.shtml, 2 pages (2015).

Clozapine. Safety Data Sheet. [online]. U.S. Pharmacopeial Convention, 2009 [retrieved on Sep. 28, 2015]. Retrieved from the Internet:<http://www.usp.org/pdf/EN/referenceStandards/msds/1142107.pdf, 6 pages (2009).

Seroquel Drug Information, 2013, Rxlist, [online]. Rxlist: The Internet Drug Index, 2013 [retrieved on Jun. 2, 2013]. Retrieved from the internet:http://www.rxlist.com/script/main/rxlist.asp?articlekey=74005&pf=3&page=1 3 pages, (2013).

* cited by examiner

FIG. 1 - In Vitro Release Profiles of Ciprofloxacin from IR and GR-1 Tablets

FIG. 3 - Normalized Cumulative Urinary Excretion of Ciprofloxacin

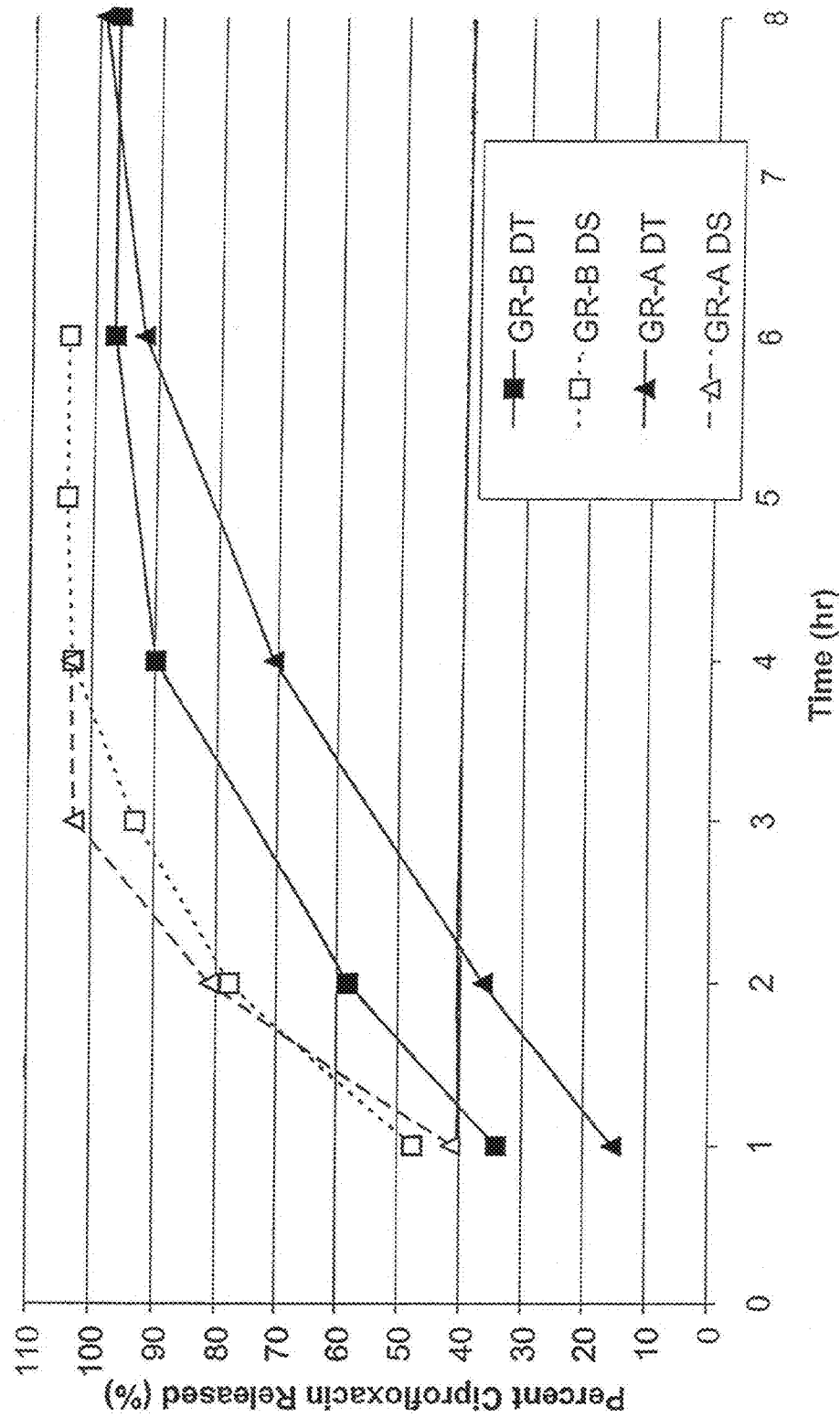

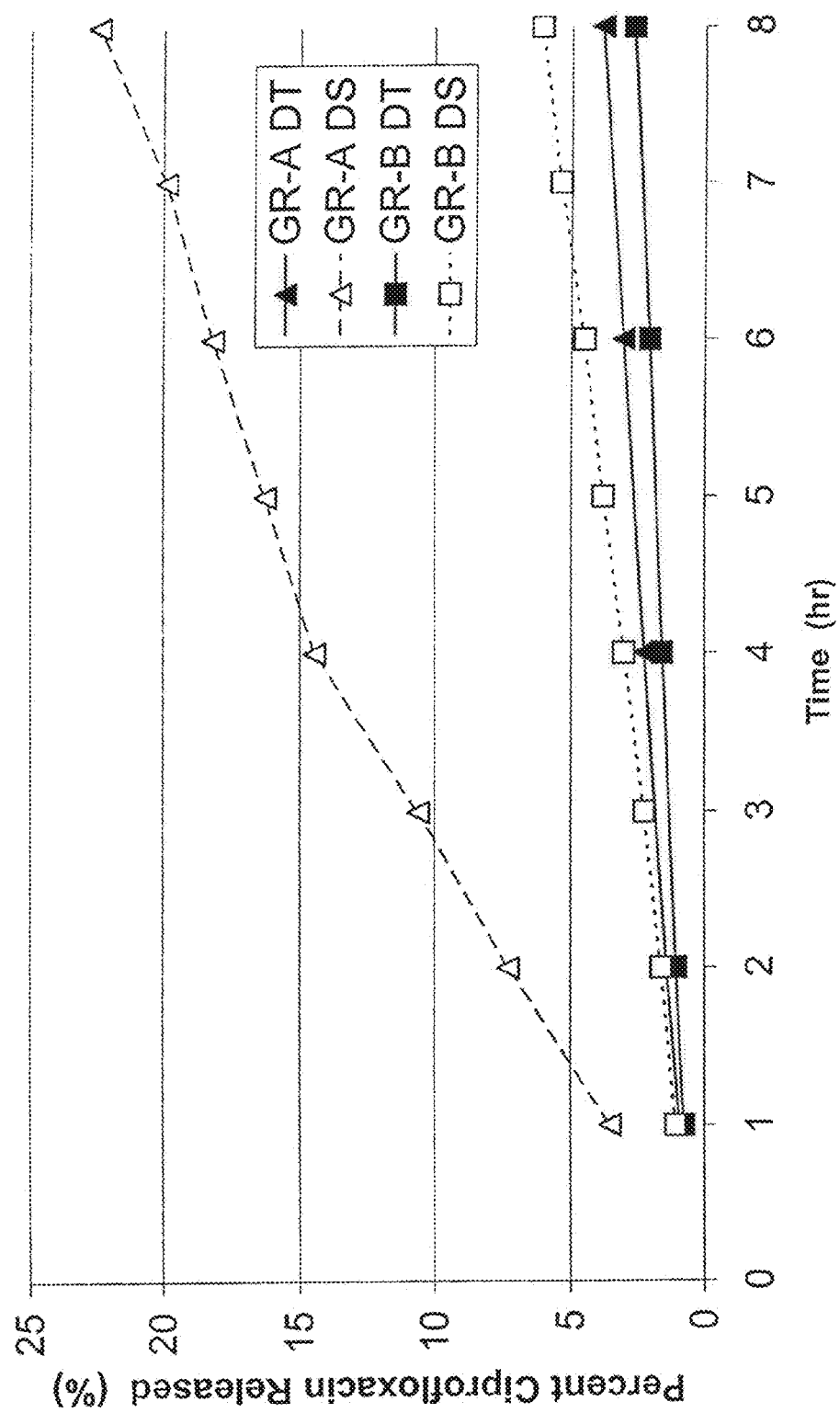

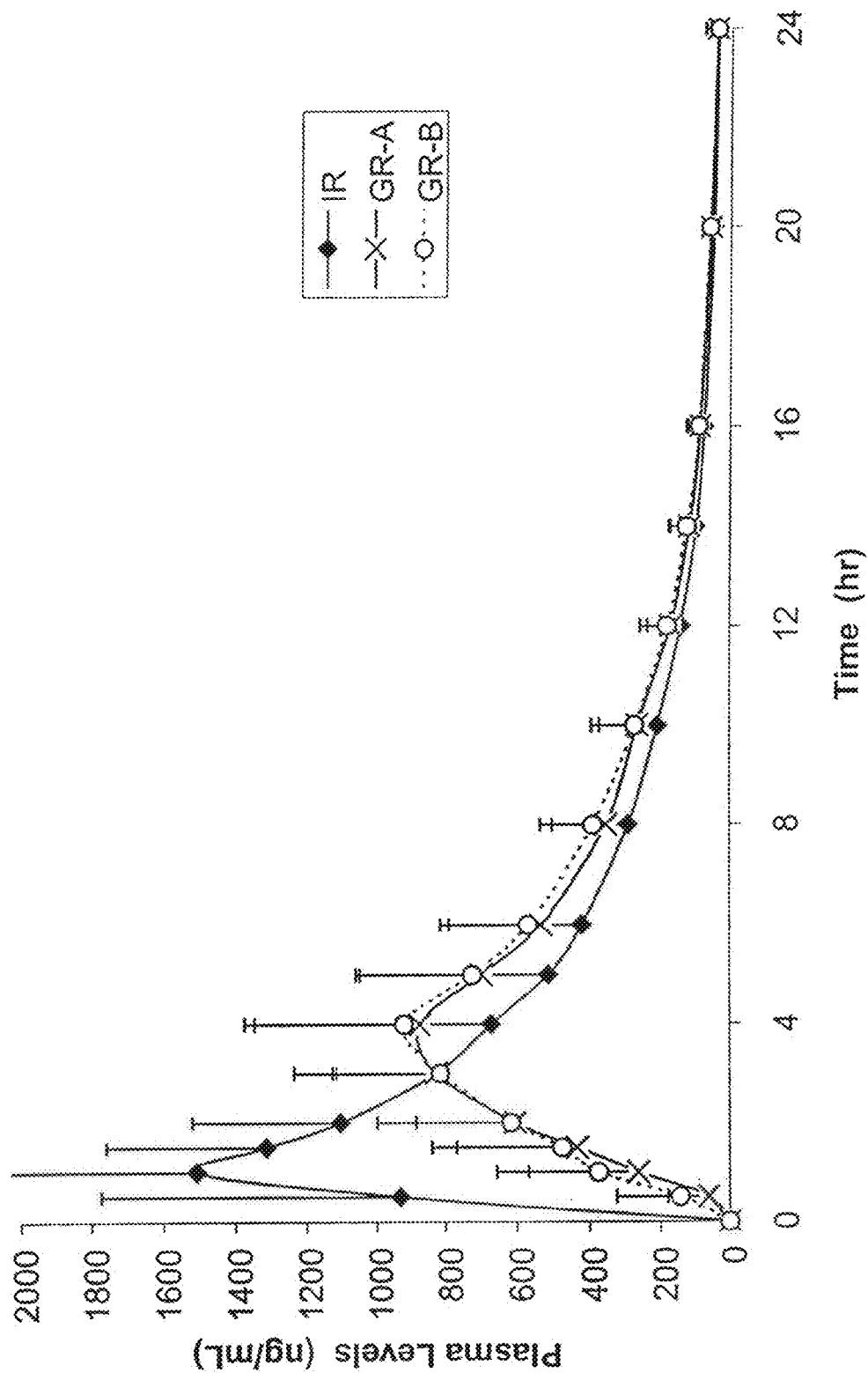
FIG. 9 - Ciprofloxacin 500 mg: GR vs. IR in Fed Mode

GASTRIC RETENTIVE ORAL DOSAGE FORM WITH RESTRICTED DRUG RELEASE IN THE LOWER GASTROINTESTINAL TRACT

CROSS REFERENCE TO RELATED APPLICATIONS

This application is a divisional of U.S. patent application Ser. No. 10/769,574, now allowed, which is a divisional of U.S. patent application Ser. No. 10/024,932, filed Dec. 18, 2001, abandoned, which is a continuation-in-part of U.S. patent application Ser. No. 10/045,816, filed on Oct. 25, 2001, abandoned, the disclosures of which are hereby incorporated by reference in their entirety.

TECHNICAL FIELD

The present invention relates generally to the field of drug delivery. More particularly, the invention relates to controlled release, gastric retentive dosage forms for oral administration, formulated so as to deliver the majority of the incorporated drug into the stomach and upper gastrointestinal tract, with restricted drug delivery in the lower gastrointestinal tract.

BACKGROUND OF THE INVENTION

Sustained release dosage forms for oral administration, designed to deliver a pharmacologically active agent over an extended time period, are well known. In particular, dosage forms that are capable of delivering drug to the stomach and gastrointestinal tract in a controlled, "sustained release" manner are described in U.S. Pat. No. 5,007,790 to Shell, U.S. Pat. No. 5,582,837 to Shell and U.S. Pat. No. 5,972,389 to Shell et al., all of common assignment herewith. The dosage forms described in the aforementioned patents are comprised of particles of a hydrophilic, water-swellable polymer with the drug dispersed therein. The polymeric particles in which the drug is dispersed absorb water, causing the particles to swell, which in turn promotes their retention in the stomach and also allows the drug contained in the particles to dissolve and then diffuse out of the particles. The polymeric particles also release drug as a result of physical erosion, i.e., degradation.

Release of certain types of pharmacologically active agents or fragments thereof into the lower gastrointestinal tract is not desirable and may be detrimental to a number of patients. Release of antibiotics into the colon, for example, may disrupt the delicate balance of the natural flora and result in conditions such as pseudomembranous colitis. Most oral dosage forms, especially controlled release dosage forms, have the potential to deliver a significant amount of drug to the lower gastrointestinal tract and colon.

It has now been discovered that erodible, swellable dosage forms akin to those described in the '790, '837 and '389 patents may be modified so that drug delivery is targeted, i.e., the active agent is primarily released in the stomach and upper gastrointestinal tract, while release in the lower gastrointestinal tract and colon is minimal.

Representative active agents with which the present invention may be used are fluoroquinolone antibiotics, i.e., fluorinated analogs of nalidixic acid. These antibiotics are active against both gram-positive and gram-negative bacteria, and are believed to exert their therapeutic effect by inhibiting bacterial topoisomerase II (DNA gyrase) and topoisomerase IV, thus blocking bacterial DNA synthesis. Fluoroquinolone antibiotics include ciprofloxacin, clinatioxacin enoxacin, gatifloxacin, grepafloxacin, levofloxaein, lomefloxacin, moxifloxacin, norfioxacin, ofloxacin, pefloxacin, sparfioxacin, trovatloxacin, and acid addition salts thereof.

Ciprofloxacin, 1-cyclopropyl-6-fluoro-1,4-dihydro-4-oxo-7-(1-piperazinyl)-3-quinolinecarboxylic acid, is available commercially from the Bayer Corporation under the trade name Cipro®. Ciprofloxacin is of particular current interest, not only for its utility in treating opportunistic bacterial infections associated with HIV (e.g., infection with *mycobacterium avium* complex, or "MAC"), urinary tract infections (including those caused by multi-drug resistant bacteria such as *Pseudomonas*), bacterial diarrhea (caused, for example, by *Shigella, Salmonella*, toxigenic *E. Coli*, or *Campylobacler*), tissue, bone and joint infections (e.g., caused by organisms such as *Enterobacter*), but also for its utility in inhibiting *Bacillus anthracis*, commonly known as "anthrax." See, for example, D'iakov et al. (1994), "Comparative Evaluation of the Effectiveness of Fluoroquinolones in Experimental Anthrax Infection," *Antibiot. Khimioter.* 39(6): 15-19; Friedlander et al. (1993), "Postexposure Prophylaxis Against Experimental Inhalation Anthrax," *J. Dis.* 167(5): 1239-1243; Kelly et al. (1992) *J. Infect. Dis.* 166(5): 1184-1187. Ciprofloxacin is rapidly and well absorbed from the gastrointestinal (G.I.) tract, with an absolute bioavailability in the range of approximately 55% to 85%, typically around 70%. With the presently available immediate release dosage form, the maximum serum concentration is attained 1-2 hours after dosing and the serum half-life is approximately 4 hours. Ciprofloxacin and associated uses, synthetic methods, and formulations are described in U.S. Pat. Nos. 4,670,444; 4,705,789; 4,808,583; 4,844,902; 4,957,922; 5,286,754; 5,695,784; and 6,136,347.

The current ciprofloxacin dosage forms are administered once every twelve hours. Since the effect of ciprofloxacin persists longer than the 4-hour half-life of the drug (Davis et al. (1996) *Drugs* 51:1019-1074), extension of the duration of the plasma profile should, in theory, enable once daily delivery. However, design of a once daily dosage form with conventional sustained release dosage forms is problematic, because ciprofloxacin is poorly absorbed in the colon (Arder et al. (1990) *Br. J. Olin. Pharmacol:* 30-39) and delivery of any antibiotic to a healthy colon may lead to enterocolitis (Schact et al. (1988) *Infection* 16:S29), as alluded to above.

There is accordingly a need in the art to provide gastric retentive dosage terms wherein drug release in the lower gastrointestinal tract and colon is restricted, and the majority of the drug dose is delivered to the stomach and upper gastrointestinal tract. The invention is useful not only in conjunction with the delivery of ciprofloxacin, fluoroquinolone antibacterial agents in general, and other antibiotics, but also with a host of active agents for which restricted delivery in the lower intestinal tract is desirable.

SUMMARY OF THE INVENTION

The present invention is directed to the aforementioned need in the art, and provides a controlled release oral dosage form for the continuous, sustained administration of a pharmacologically active agent to the upper G.I. tract of a patient in whom the fed mode as been induced. The majority of the agent is delivered, on an extended release basis, to the stomach, duodenum and upper regions of the small intestine, with drug delivery in the lower gastrointestinal tract and colon substantially restricted. The dosage form comprises a matrix of a biocompatible, hydrophilic, erodible polymer with an active agent incorporated therein, with the active agent preferably representing at least about 60% by volume of the dosage form, wherein the polymer is one that both swells in the presence of water and gradually erodes over a time period of hours, with swelling and erosion commencing upon contact with gastric fluid.

In order to deliver the majority of the drug dose to the stomach and upper G.I. tract and avoid or at least minimize delivery of the drug to the lower intestine and colon, the drug release period should be less than that of the sum of the mean gastric emptying time and the transit time through the small intestine. For drugs having low aqueous solubility, this means that the duration of erosion—which is approximately equivalent to the drug release period with such active agents—should be less than that of the sum of the mean gastric emptying time and the transit time through the small intestine. The dosage forms of the invention are particularly adapted for delivery of active agents whose aqueous solubility decreases as pH increases, such as ciprofloxacin and other fluoroquinolone antibiotics, such that any active agent remaining in the dosage form upon passage from the acidic region of the stomach and upper G.I. tract into the much more basic lower G.I. tract will not be in solution, and, therefore, not available for absorption.

Further, in order to minimize variability in the rate of absorption, $C_{max}$ and $t_{max}$ from patient to patient, it is necessary to minimize the variability in the rate of drug release from gastric retentive dosage forms. The ratio of erosion rate "ER" obtained in vitro using a disintegration test (i.e., the rate of drug release as a result of dosage form erosion or disintegration) to the dissolution rate "DR" obtained in vitro using a dissolution test (i.e., the rate of drug release as a result of swelling, dissolution, and diffusion out of the matrix), can be adjusted in the present dosage forms, not only to optimize the site of drug delivery, but also to provide a dosage form wherein the dependency of the release profile on mechanical and hydrodynamic forces is minimized, thereby, in turn, minimizing variability in the rate of drug release. The ratio of the aforementioned ER to DR values obtained in vitro should generally be in the range of about 1, 2:1 to 5:1, preferably about 1.2:1 to 3:1, more preferably about 1.3:1 to 2:1, and most preferably about 1.5:1 to 2:1. Optimization of the ER to DR ratio may be controlled by adjusting the size and/or shape of the dosage form, by selecting matrix polymers having particular swelling and erosion rates, by increasing or decreasing drug loading, and by using additives such as disintegrants and solubilizers. For example, the rate of diffusion of dissolved active agent out of the matrix the DR) can be slowed relative to the rate at which the active agent is released via polymer erosion (the ER) by increasing the volume fraction of drug and selecting a polymer that will erode faster than it will swell.

These dosage forms can minimize or even eliminate problems such as the overgrowth of detrimental intestinal flora resulting from drugs that are toxic to normal intestinal flora, by delivering the bulk of the drug dose to the upper G.I. tract and allowing little or no drug to reach the lower G.I. tract or colon. The dosage forms can also prevent chemical degradation of drugs by intestinal enzymes, as alluded to above, loss of bioavailability of a drug due to its leaving the acidic environment of the stomach, and chemical degradation of a drug in the neutral to alkaline environment of the gastrointestinal tract. Finally, the dosage harm can extend the drug delivery period so as to allow less frequent administration. For example, the invention enables preparation of once-a-day dosage forms for the administration of fluoroquinolone antibiotics such as ciprofloxacin, which are currently administered at least twice daily.

When used to administer drugs that are highly soluble in aqueous acid, the active agent may be contained within a vesicle that prevents a too rapid release rate in the acidic environment of the upper G.I. tract. Suitable vesicles include, but are not limited to, liposomes and nanoparticles, including nanocrystals, nanospheres and nanocapsules.

In a further embodiment of this invention, the dosage harm is a bilayer tablet, a trilayer tablet, or a shell-and-core tablet, with bilayer and trilayer tablets preferred. With the bilayer tablet, one layer contains drug and is comprised of a polymer that is primarily erodible, and a second, swellable layer may contain the same drug, a different drug, or no drug. The inaction of the swelling layer is to provide sufficient particle size throughout the entire period of drug delivery to promote gastric retention in the fed mode. With the trilayer tablet, the outer layers contain drug and are comprised of a polymer that is primarily erodible, while the middle layer is swellable.

The invention additionally provides a method for using these dosage forms to administer drugs on an extended basis to the stomach, duodenum and upper sections of the small intestine, while minimizing delivery to the lower G.I. tract and colon, as well as a method for preparing the dosage forms so as achieve the aforementioned targeted delivery profile while minimizing patient-to-patient variability. The latter method involves preparing the dosage form with a predetermined ratio of disintegration release ER to dissolution release DR. The ER may be evaluated using any suitable disintegration test that is predictive of drug release behavior in vivo, although a particularly preferred such test is the standard USP Disintegration Test as set forth in USP 24-NF 19, Supplement 4, Section 701, published by the United States Pharmacopeia & National Formulary in 2001, or a modification of the standard test. The pertinent information obtained using the disintegration test is the "disintegration time," a term that is used interchangeably herein with the terms "erosion rate," "erosion release," "disintegration rate," and "disintegration release," and generally refers to the time for complete disintegration of the dosage form to occur, wherein "complete disintegration" is as defined as the state in which less than 10%, preferably less than 5%, of the original dosage form (or the active agent-containing layer in a bilayer or trilayer tablet) remains visible. If the test is stopped prior to complete disintegration, the fraction of the dosage form that has disintegrated is noted along with the time of the monitoring period for example, the ER may be reported as "40% released at 4 hours," "80% released at 8 hours," or the like). The DR, on the other hand, is generally evaluated using USP Dissolution Test equipment and the standard USP Dissolution Test as set forth in USP 24-NF 19, Supplement 4, Section 711, which calls for immersion of a dosage in a specified solvent at 37° C., for a given time period, using either a basket stirring element or a paddle stirring element (respectively referred to as "Apparatus 1" and "Apparatus 2" in USP 24-NF 19). At regular time intervals, a sample of the solvent is withdrawn and the drug concentration therein determined, e.g., by HPLC. The pertinent information obtained using the dissolution test is the "dissolution release," a term that is used interchangeably herein with the terms "dissolution rate," "dissolution release," "swelling rate," and "diffusion rate," and refers to the time for complete release of drug to occur, wherein "complete release" is as defined as the state in which greater than 90%, preferably greater than 95% of the drug has been released. As with the ER, if the test is stopped prior to complete release, the fraction of drug released is noted along with the time of the monitoring period.

BRIEF DESCRIPTION OF THE DRAWINGS

FIGS. 7 and 8 are plots showing the dissolution and disintegration profiles at pH 1 and 6.8, respectively, obtained in vitro for the gastric retentive dosage forms evaluated in Example 3.

FIG. 9 is a plot of plasma level versus time for an in vivo study carried out with ciprofloxacin HCl dosage forms, as described in Example 4.

DETAILED DESCRIPTION OF THE INVENTION

I. Definitions and Overview

Figure 1:
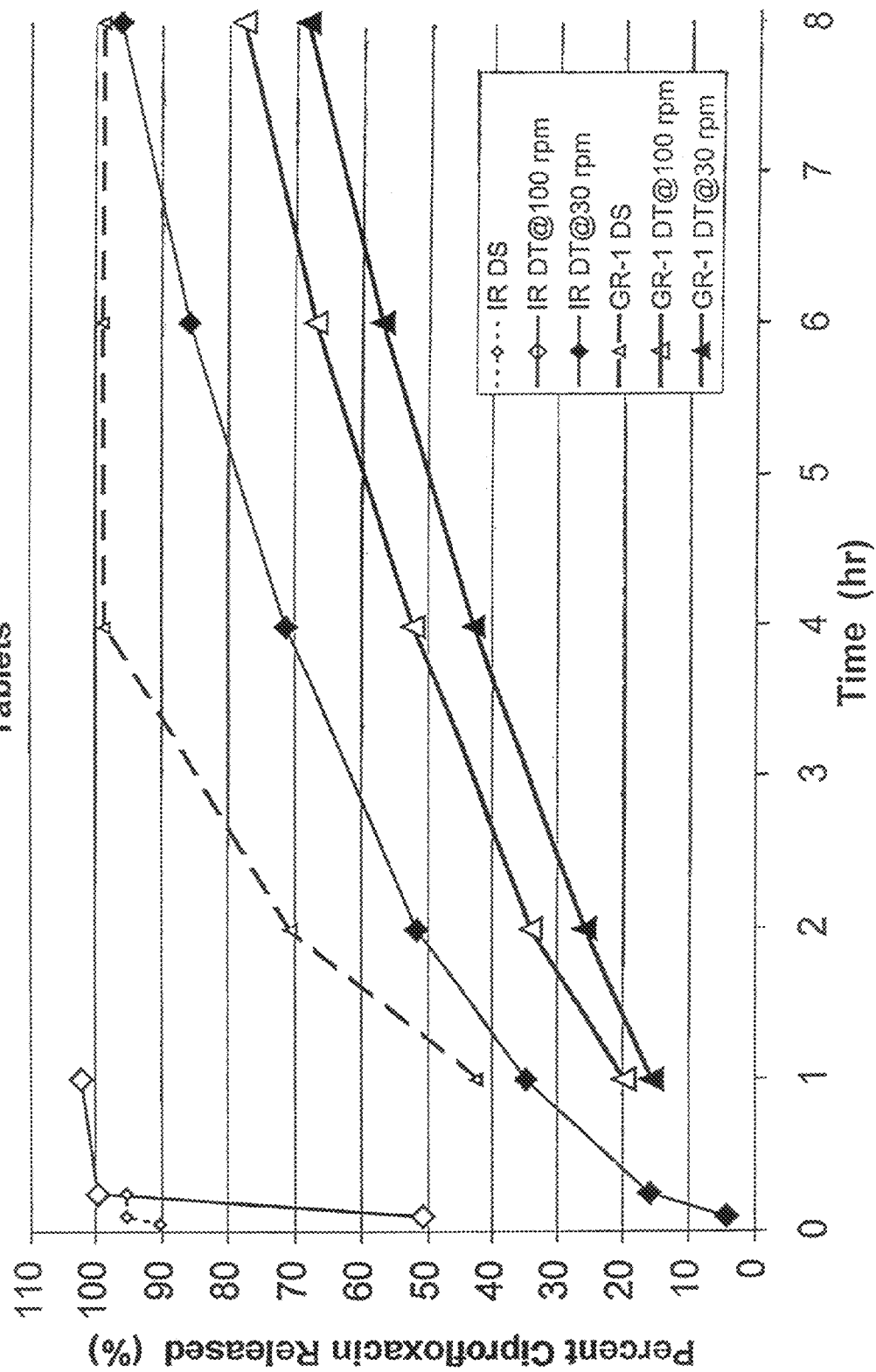
FIGS. 1 and 2 are plots showing the in vitro release characteristics of the four dosage forms evaluated in Example 1, evaluated using both a disintegration test and a dissolution test.

Before describing the present invention in detail, it is to be understood that this invention is not limited to specific active agents, dosage forms, dosing regimens, or the like, as such may vary. It is also to be understood that the terminology used herein is for the purpose of describing particular embodiments only, and is not intended to be limiting.

It must be noted that as used in this specification and the appended claims, the singular forms "a," "an" and "the" include plural referents unless the context clearly dictates otherwise. Thus, for example, reference to "an active agent" or "a pharmacologically active agent" includes a single active agent as well a two or more different active agents in combination, reference to "a polymer" includes mixtures of two or more polymers as well as a single polymer, and the like.

In describing and claiming the present invention, the following terminology will be used in accordance with the definitions set out below.

The terms "drug," "active agent," and "pharmacologically active agent" are used interchangeably herein to refer to any chemical compound, complex or composition that is suitable for oral administration and that has a beneficial biological effect, preferably a therapeutic effect in the treatment of a disease or abnormal physiological condition. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent" and "drug" are used, then, or when a particular active agent is specifically identified, it is to be understood that applicants intend to include the active agent per se as well as pharmaceutically acceptable, pharmacologically active salts, esters, amides, prodrugs, metabolites, analogs, etc.

The term "dosage form" denotes any form of a pharmaceutical composition that contains an amount of active agent sufficient to achieve a therapeutic effect with a single administration. When the formulation is a tablet or capsule, the dosage form is usually one such tablet or capsule. The frequency of administration that will provide the most effective results in an efficient manner without overdosing will vary with: (1) the characteristics of the particular drug, including both its pharmacological characteristics and its physical characteristics, such as solubility; (2) the characteristics of the swellable matrix, such as its permeability; and (3) the relative amounts of the drug and polymer. In most cases, the dosage form will be such that effective results will be achieved with administration no more frequently than once every eight hours, preferably no more frequently than once every twelve hours, and even more preferably no more frequently than once every twenty-four hours.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual by inhibiting or causing regression of a disorder or disease.

By an "effective" amount or a "therapeutically effective amount" of a drug or pharmacologically active agent is meant a nontoxic but sufficient amount of the drug or agent to provide the desired effect.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained, "Pharmacologically active" (or simply "active") as in a "pharmacologically active" derivative, refers to a derivative having the same type of pharmacological activity as the parent compound and approximately equivalent in degree. When the term "pharmaceutically acceptable" is used to refer to a derivative (e.g., a salt) of an active agent, it is to be understood that the compound is pharmacologically active as well. When the term, "pharmaceutically acceptable" is used to refer to an excipient, it implies that the excipient has met the required standards of toxicological and manufacturing testing or that it is on the Inactive ingredient Guide prepared by the FDA.

The term "biocompatible" is used interchangeably with the term "pharmaceutically acceptable."

The term "soluble," as used herein, refers to a drug having an aqueous solubility (measured in water at 20° C.) greater than 10%, preferably greater than 35%, by weight. The terms "slightly soluble" and "sparingly soluble" refer to a drug having an aqueous solubility (measured at 20° C.) in the range of 2% to 10% by weight, while drugs having an aqueous solubility in the range of 0.001% to less than 2% by weight are referred to as "substantially insoluble."

The term "vesicle," as used herein, refers to a small (usually 0.01 to 1.0 mm), usually spherical, membrane-bound structure that may contain or be composed of either lipoidal or aqueous material, or both. Suitable vesicles include, but are not limited to, liposomes, nanoparticles, and microspheres composed of amino acids. While some of these particles, especially nanoparticles and microspheres, need not be membrane-bound structures, for the purposes of the present invention, they are encompassed by the term "vesicle."

The term "controlled release" is intended to refer to any drug-containing formulation in which release of the drug is not immediate, i.e., with a "controlled release" formulation, oral administration does not result in immediate release of the drug into an absorption pool. The term is used interchangeably with "nonimmediate release" as defined in *Remington: The Science and Practice of Pharmacy, Nineteenth Ed* (Easton, Pa.: Mack Publishing Company, 1995). As discussed therein, immediate and nonimmediate release can be defined kinetically by reference to the following equation:

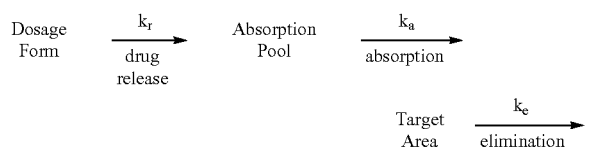

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant ka. For controlled release formulations, the opposite is true, i.e., $k_r \ll k_a$, such that the rate of release of drug from the dosage form is the rate-limiting step in the delivery of the drug to the target area. It should be noted that this simplified model uses a single first order rate constant for release and absorption, and that the controlled release kinetics with any particular dosage form may be much for complicated. In general, however, the term "controlled release" as used herein includes any nonimmediate release formulation.

The term "sustained release" is used in its conventional sense to refer to a drug formulation that provides for gradual release of a drug over an extended period of time, and that preferably, although not necessarily, results in substantially constant blood levels of a drug over an extended time period.

The terms "hydrophilic" and "hydrophobic" are generally defined in terms of a partition coefficient P, which is the ratio of the equilibrium concentration of a compound in an organic phase to that in an aqueous phase. A hydrophilic compound has a P value less than 1.0, typically less than about 0.5, where P is the partition coefficient of the compound between octanol and water, while hydrophobic compounds will generally have a P greater than about 1.0, typically greater than about 5.0. The polymeric carriers herein are hydrophilic, and thus compatible with aqueous fluids such as those present in the human body.

The term "polymer" as used herein refers to a molecule containing a plurality of covalently attached monomer units, and includes branched, dendrimeric and star polymers as well as linear polymers. The term also includes both homopolymers and copolymers, e.g., random copolymers, block copolymers and graft copolymers, as well as uncrosslinked polymers and slightly to moderately to substantially crosslinked polymers.

The terms "swellable" and "bioerodible" (or simply "erodible") are used to refer to the polymers used in the present dosage forms, with "swellable" polymers being those that are capable of absorbing water and physically swelling as a result, with the extent to which a polymer can swell being determined by the degree of crosslinking, and "bioerodible" or "erodible" polymers referring to polymers that slowly dissolve and/or gradually hydrolyze in an aqueous fluid, and/or that physically erodes as a result of movement within the stomach or gastrointestinal tract.

The in vivo "release rate" and in vivo "release profile" refer to the time it takes for the orally administered dosage form, or the active agent-containing layer of a bilayer or trilayer tablet (again, administered when the stomach is in the fed mode) to be reduced to 0-10%, preferably 0-5%, of its original size, as may be observed visually using NMR shift reagents or paramagnetic species, radio-opaque species or markers, or radiolabels. Unless otherwise indicated herein, all references to in vivo tests and in vivo results refer to results obtained upon oral administration of a dosage form with food, such that the stomach is in the fed mode.

The term "fed mode," as used herein, refers to a state which is typically induced in a patient by the presence of food in the stomach, the food giving rise to two signals, one that is said to stem from stomach distension and the other a chemical signal based on food in the stomach. It has been determined that once the fed mode has been induced, larger particles are retained in the stomach for a longer period of time than smaller particles. Thus, the fed mode is typically induced in a patient by the presence of food in the stomach.

In the normal digestive process, the passage of matter through the stomach is delayed by a physiological condition that is variously referred to as the digestive mode, the postprandial mode, or the "fed mode." Between fed modes, the stomach is in the interdigestive or "fasting" mode. The difference between the two modes lies in the pattern of gastroduodenal motor activity.

In the fasting mode, the stomach exhibits a cyclic activity called the interdigestive migrating motor complex ("IMMC"). This activity occurs in four phases:

Phase I, which lasts 45 to 60 minutes, is the most quiescent, with the stomach experiencing few or no contractions;

Phase II, characterized by sweeping contractions occurring in an irregular intermittent pattern and gradually increasing in magnitude;

Phase III, consisting of intense bursts of peristaltic waves in both the stomach and the small bowel, lasting for about 5 to 15 minutes; and Phase IV is a transition period of decreasing activity which lasts until the next cycle begins.

The total cycle time for all four phases is approximately 90 minutes. The greatest activity occurs in Phase III, when powerful peristaltic waves sweep the swallowed saliva, gastric secretions, food particles, and particulate debris, out of the stomach and into the small intestine and colon. Phase III thus serves as an intestinal housekeeper, preparing the upper tract for the next meal and preventing bacterial overgrowth.

The fed mode is initiated by nutritive materials entering the stomach upon the ingestion of food. Initiation is accompanied by a rapid and profound change in the motor pattern of the upper gastrointestinal tract, over a period of 30 seconds to one minute. The change is observed almost simultaneously at all sites along the G.I. tract and occurs before the stomach contents have reached the distal small intestine. Once the fed mode is established, the stomach generates 3-4 continuous and regular contractions per minute, similar to those of the fasting mode but with about half the amplitude. The pylorus is partially open, causing a sieving effect in which liquids and small particles flow continuously from the stomach into the intestine while indigestible particles greater in size than the pyloric opening are retropelled and retained in the stomach. This sieving effect thus causes the stomach to retain particles exceeding about 1 cm in size for approximately 4 to 6 hours.

Accordingly, the present drug delivery systems are used to administer a drug to the fed stomach and upper G.I. tract while minimizing drug release in the lower G.I. tract and colon. The method is particularly useful in conjunction with the delivery of drugs that are toxic to normal intestinal flora or are used to treat a local condition or disorder, e.g., a stomach ulcer. The dosage forms, having an optimized ratio of erosion rate to dissolution rate and, preferably, although not necessarily, a volume fraction of the drug of at least 60%, provide for effective delivery of drugs to the upper G.I. tract, with delivery to the lower G.I. tract and colon restricted and the drug delivery period in the upper G.I. tract extended relative to the delivery period associated with immediate release and prior gastric retentive dosage forms. The dosage forms are particularly suited to administration of drugs whose aqueous solubility decreases with increasing pH, such that the drug is substantially more soluble in the acidic environment of the stomach than in the more basic regions of the lower G.I. tract.

The dosage forms of the invention are comprised of at least one biocompatible, hydrophilic, erodible polymer with a drug dispersed therein. The swelling properties of the polymer(s) are important insofar as they promote gastric retention of the dosage forms in the fed stomach. For drug delivery to the stomach and upper G.I. tract, a polymer is used that (i) swells unrestrained dimensionally via imbibition of gastric fluid to increase the size of the particles to promote gastric retention within the stomach of a patient in whom the fed mode has been induced, (ii) gradually erodes over a time period of hours, with the erosion commencing upon contact with the gastric fluid, and (iii) releases the drug to the stomach, duodenum and upper G.I. tract at a rate that, in general, is primarily dependent on the erosion rate. That is, with respect to the latter requirement, preferred dosage forms have an erosion rate that is slightly faster than the swelling rate, such that drug release from the dosage form is primarily controlled by polymer erosion than by polymer swelling.

II. Optimization Using Disintegration and Dissolution Tests

The preferred composition of a dosage form of the invention gives rise not only to the desired drug release profile in vivo, i.e., a release profile wherein the majority of the drug dose is delivered to the upper G.I. tract with restricted delivery to the lower G.I. tract, but also effectively minimizes patient-to-patient variability in release profile. One of the ways the invention accomplishes this is by providing a dosage form whose ER to DR is optimized such that the ratio of ER to DR is in the range of about 1.2:1 to 5:1, preferably about 1.2:1 to 3:1, more preferably about 1.3:1 to 2:1, and most preferably about 1.5:1 to 2:1.

The ER may be evaluated using any suitable disintegration test, although a particularly preferred such test is the standard USP Disintegration Test as set forth in USP 24-NF 19, Supplement 4, Section 701, published by the United States Pharmacopeia National Formulary in 2001, or a modification of the standard test. As explained in the aforementioned section of USP 24-NF 19, the USP Disintegration apparatus consists of a basket-rack assembly, a 1000-ml beaker, 142 to 148 mm in height and having an outside diameter of 103 to 108 mm, thermostatic arrangement for heating an immersion fluid between 35° C. and 39° C., and a device for raising and lowering the basket in the immersion fluid at a constant frequency rate between 29 and 32 cycles pet minute through a distance of 5.3 cm to 5.7 cm. The time required for the upward and downward strokes is the same, and the volume of the fluid in the vessel is such that the wire mesh of the basket remains at least 2.5 cm below the fluid surface on the upward stroke, and should not descend to within less than 2.5 cm of the bottom of the vessel on the downward stroke. There should be no appreciable horizontal movement of the basket rack assembly; the assembly moves solely in a vertical direction, along its axis. The basket-rack assembly consists of six open-ended transparent tubes, each having dimensions specified in the aforementioned section of USP 24-NF 19; the tubes are held in a vertical position by two plastic plates, with six holes equidistance from the center of the plate and equally spaced from one another. Attached to the undersurface of the lower plate is a woven stainless steel wire mesh. A suitable means is provided to suspend the basket-rack assembly from a raising and lowering device.

Accordingly, the USP Disintegration Test is conducted using the above-described test equipment by placing the dosage form to be tested in each basket-rack assembly, immersing the assembly in a specified fluid at a temperature between 35° C. and 39° C. for a given time period, and raising and lowering the basket in the immersion fluid through a distance of about 5.5 cm at a frequency of about 30 cycles per minute. The dosage forms are visually inspected at specified times for complete disintegration. The particularly preferred disintegration test used in conjunction with the invention is a modification of the standard USP Disintegration Test wherein one to three tablets are tested per basket, an extended monitoring time is used, e.g., a four-hour to twenty-four-hour time period, generally a two-hour to twenty-four hour period, preferably a four- to eight-hour time period, and wherein a thin plastic disk (9.5±0.15 mm in thickness, 20.7±0.15 mm in diameter) is placed on each dosage form (noted as optional in Section 701 of USP 24-NF 19).

The DR is evaluated using a dissolution test that is predictive of drug release behavior, with the DSP Disintegration Test (as set forth in USP 24-NF 19, Supplement 4, Section 711) or a modification of the standard test. Either of two devices is used in the USP Disintegration Test, "Apparatus 1" and "Apparatus 2." Apparatus 1 consists of a covered vessel, a motor, a metallic drive shaft, and a cylindrical basket that serves a stirring element. The vessel is made of a material that does not sorb, react, or interfere with the dosage forms to be tested, with glass and other inert, transparent materials preferred. The vessel is partially immersed in a water bath or placed in a heating jacket, such that the temperature inside the vessel is maintained at 37±0.5° C. during the test, with the water in the water bath, if used, kept inconstant, smooth motion by the rotating basket. A device that allows for observation of the dosage form during the test is preferred. The vessel is cylindrical, with a hemispherical bottom and one of the following dimensions: height of 160 mm to 210 mm, inside diameter of 98 mm to 106 mm, capacity of 1 liter; height of 280 mm to 300 mm, inside diameter of 98 mm to 106 mm, capacity of 2 liters; an height of 280 mm to 300 mm, inside diameter of 145 mm to 155 mm, capacity of 4 liters. The shaft is positioned so that the distance between the shaft axis and the vertical axis of the vessel is less than 2 mm, at all points, thus ensuring smooth rotation without significant wobble. A speed-regulating device is used that allows the shaft rotation speed to be controlled.

USP Dissolution Apparatus 2 is similar to that of Apparatus 1, except that the rotating basket is replaced with a paddle formed from a blade and a shaft, with the blade and shaft integrated so as to comprise a single structural entity. The paddle may be metallic (composed of, for example, 303 stainless steel) or it may be comprised of some other suitably inert, rigid material. A distance of 25±2 mm is maintained between the blade and the inside bottom of the vessel, during the test. The dosage unit is allowed to sink to the bottom of the vessel before rotation of the blade is started. A small, loose piece of nonreactive material (such as not more than a few turns of a wire helix) may be attached to dosage units that would otherwise float.

The preferred dissolution apparatus used herein is the USP Apparatus 1, using standard 40-mesh rotating baskets, a basket rotation speed of 100 rpm, a 1 liter vessel containing a dissolution medium specified in the individual USP monograph for the particular active agent and type of dosage form being tested (e.g., 900 mL deionized (DI) water for sustained release ciprofloxacin tablets) as the dissolution medium, anti-evaporation covers, and a Distek Dissolution System 2100B USP Bath or equivalent. The dissolution test is carried out by assembling the apparatus as described above and as explained in detail in Section 711 of USP 24-NF 19, filling the 1-liter vessels with 900 mL deionized (DI) water as the dissolution medium, and equilibrating the DI water to 37±0.5° C. Each dosage form is weighed and placed in into a dry 40-mesh basket, and then lowered into the DI water at to. Samples are removed as 5.0 mL aliquots at various time points, typically although not necessarily at 1, 2, 4, 6 and 8 hours, from a zone midway between the surface of the DI water and the top of the rotating basket, not less than 1 cm from the vessel wall. Quantitation may then be performed using any suitable technique, with reverse phase liquid chromatography and an ultraviolet detection system.

To optimize the ER-to-DR ratio for a particular drug, various dosage forms can be prepared and evaluated for their ER and DR using the above tests. That is, one or more matrix polymers are selected along with an active agent to be administered, and different dosage forms are prepared using different matrix polymers and/or active agents, matrix polymers of different molecular weights, matrix polymers cross-linked to different degrees, and/or different amounts of different components, such as lubricants, solubilizers, disintegrants, and the like. Those dosage Forms that exhibit an optimized ER-to-DR ratio, i.e., in the range of about 1.2:1 to 5:1, preferably about 1.2:1 to 3:1, more preferably about 1.3:1 to 2:1, and most preferably about 1.5:1 to 2:1.

III. Swellable, Bioerodible Polymers

The polymer used in the dosage forms of the present invention should not release the drug at too rapid a rate so as to result in a drug overdose or rapid passage into and through the upper gastrointestinal tract (i.e., in less than about four hours), nor should the polymer release drug too slowly to achieve the desired biological effect. That is, the majority of the drug dose should be delivered in the stomach and upper G.I. tract, but drug release in the stomach and upper G.I. tract should still occur over an extended time period. Polymers that permit a rate of drug release that achieves the requisite pharmacokinetics for a desired duration, as determined using the USP Dissolution and Disintegration Tests, are selected for use in the dosage forms of the present invention.

Polymers suitable for use in the present invention are those that both swell upon absorption of gastric fluid and gradually erode over a time period of hours. Erosion initiates simultaneously with the swelling process, upon contact of the surface of the dosage form with gastric fluid. Erosion reflects the dissolution of the polymer beyond the polymer gel-solution interface where the polymer has become sufficiently dilute that it can be transported away from the dosage form by diffusion or convection. This may also depend on the hydrodynamic and mechanical forces present in the gastrointestinal tract during the digestive process. While swelling and erosion occur at the same time, it is preferred herein that drug release should be erosion-controlled, meaning that the selected polymer should be such that complete drug release occurs primarily as a result of erosion rather than swelling and dissolution. However, swelling should take place at a rate that is sufficiently fast to allow the tablet to be retained in the fed stomach for a time period in the range of about 2-12 hours, preferably in the range of about 4-9 hours. At minimum, for an erosional gastric retentive dosage form, there should be an extended period during which the dosage form maintains its size before it is diminished by erosion.

Suitable polymers for use in the present dosage forms may be linear, branched, dendrimeric, or star polymers, and include synthetic hydrophilic polymers as well as semi-synthetic and naturally occurring hydrophilic polymers. The polymers may be homopolymers or copolymers, if copolymers, either random copolymers, block copolymers or graft copolymers. Synthetic hydrophilic polymers useful herein include, but are not limited to:

polyalkylene oxides, particularly poly(ethylene oxide), polyethylene glycol and poly(ethylene oxide)-poly(propylene oxide) copolymers;

cellulosic polymers;

acrylic acid and methacrylic acid polymers, copolymers and esters thereof, preferably formed from acrylic acid, methacrylic acid, methyl acrylate, ethyl acrylate, methyl methacrylate, ethyl methacrylate, and copolymers thereof with each other or with additional acrylate species such as aminoethyl acrylate;

maleic anhydride copolymers;

polymaleic acid;

poly(acrylamides) such as polyacrylamide per se, poly (methacrylamide), poly(dimethylacrylamide), and poly(N-isopropyl-acrylamide);

poly(olefinic alcohol)s such as poly(vinyl alcohol);

poly(N-vinyl lactams) such as polyvinyl pyrrolidone), poly(N-vinyl caprolactam), and copolymers thereof;

polyols such as glycerol, polyglycerol (particularly highly branched polyglycerol), propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol;

polyoxyethylated sorbitol and polyoxyethylated glucose;

polyoxazolines, including poly(methyloxazoline) and poly(ethyloxazoline);

polyvinyl amines;

polyvinylacetates, including polyvinylacetate per seas well as ethylene-vinyl acetate copolymers, polyvinyl acetate phthalate, and the like;

polyimines, such as polyethyleneimine;

starch and starch-based polymers;

polyurethane hydrogels;
chitosan;
polysaccharide gums;
zein; and
shellac, ammoniated shellac, shellac-acetyl alcohol, and shellac n-butyl stearate.

The term "cellulosic polymer" is used herein to denote a linear polymer of anhydroglucose. Cellulosic polymers that can be used advantageously in the present dosage forms include, without limitation, hydroxymethylcellulose, hydroxypropylcellulose, hydroxyethylcellulose, hydroxypropyl methylcellulose, methylcellulose, ethylcellulose, cellulose acetate, cellulose acetate phthalate, cellulose acetate trimellitate, hydroxypropyl methylcellulose phthalate, hydroxypropylcellulose phthalate, cellulose hexahydrophthalate, cellulose acetate hexahydrophthalate, carboxymethylcellulose, carboxymethylcellulose sodium, and microcrystalline cellulose. Preferred cellulosic polymers are alkyl-substituted cellulosic polymers that ultimately dissolve in the G.I. tract in a predictably delayed manner. Preferred alkylsubstituted cellulose derivatives are those substituted with alkyl groups of 1 to 3 carbon atoms each. Examples are methylcellulose, hydroxymethylcellulose, hydroxyethylcellulose, hydroxypropylcellulose, hydroxypropyl methylcellulose, and carboxymethylcellulose. In terms of their viscosities, one class of preferred alkyl-substituted celluloses includes those whose viscosity is within the range of about 50 to about 110,000 centipoise as a 2% aqueous solution at 20° C. Another class includes those whose viscosity is within the range of about 800 to about 6,000 centipoise as a 1% aqueous solution at 20° C. Particularly preferred alkyl-substituted celluloses are hydroxyethylcellulose and hydroxypropylmethylcellulose. A presently preferred hydroxyethylcellulose is NATRASOL® 250HX NF (National Formulary), available from Aqualon Company, Wilmington, Del., USA.

Polyalkylene oxides are the preferred polymers herein, and the polyalkylene oxides that are of greatest utility are those having the properties described above for alkyl substituted cellulose polymers. A particularly preferred polyalkylene oxide is poly(ethylene oxide), which term is used herein to denote a linear polymer of unsubstituted ethylene oxide. Polyethylene oxide)s are often characterized by their viscosity in solution. For purposes of this invention, a preferred viscosity range is about 50 to about 2,000,000 centipoise for a 2% aqueous solution at 20° C. Preferred poly(ethylene oxide)s are Polyox® 303, Polyox® Coag, Polyox® 301, Polyox® WSR N-60K, Polyox® WSR 1105 and Polyox® WSR N-80, having number average molecular weights of 7 million, 5 million, 4 million, 2 million, 900,000 and 200,000, respectively, all products of Union Carbide Chemicals and Plastics Company Inc. of Danbury, Conn., USA.

Polysaccharide gums, both natural and modified (semi-synthetic) can be used. Examples are dextran, xanthan gum, gellan gum, welan gum and rhamsan gum. Xanthan gum is preferred.

Crosslinked polyacrylic acids of greatest utility are those whose properties are the same as those described above for alkyl-substituted cellulose and polyalkylene oxide polymers. Preferred crosslinked polyacrylic acids are those with a viscosity ranging from about 4,000 to about 40,000 centipoise for a 1% aqueous solution at 25° C. Three presently preferred examples are CARBOPOL® NF grades 971P, 974P and 934P (BE Goodrich Co., Specialty Polymers and Chemicals Div., Cleveland, Ohio, USA). Further examples are polymers known as WATER LOCK®, which are starch/acrylates/acrylamide copolymers available from Grain Processing Corporation, Muscatine, Iowa, USA.

Suitable polymers also include naturally occurring hydrophilic polymers such as, by way of example, proteins such as collagen, fibronectin, albumins, globulins, fibrinogen, fibrin and thrombin; aminated polysaccharides, particularly the glycosaminoglycans, e.g., hyaluronic acid, chitin, chondroitin sulfate A, B, or C, keratin sulfate, keratosulfate and heparin; guar gum; xanthan gum; carageenan; alginates; pectin; and activated polysaccharides such as dextran and starches.

The aforementioned list of polymers is not exhaustive, and a variety of other synthetic hydrophilic polymers may be used, as will be appreciated by those skilled in the art.

The polymer may include biodegradable segments and blocks, either distributed throughout the polymer's molecular structure or present as a single block, as in a block copolymer. Biodegradable segments are those that degrade so as to break covalent bonds. Typically, biodegradable segments are segments that are hydrolyzed in the presence of water. Biodegradable segments may be composed of small molecular segments such as ester linkages, anhydride linkages, ortho ester linkages, ortho carbonate linkages, amide linkages, phosphonate linkages, etc.

Any polymer or polymers of the matrix may also be crosslinked, with the degree of crosslinking directly affecting the rate of polymer swelling as well as the erosion rate. That is, a polymer having a higher degree of crosslinking will exhibit less swelling and slower erosion than a polymer having a lower degree of crosslinking. Crosslinked polymers may be prepared using the above-mentioned exemplary polymers using conventional crosslinking procedures (e.g., chemical crosslinking with an added crosslinking agent, photolytically induced crosslinking, etc.), or the polymers may be obtained commercially in crosslinked form.

The water-swellable polymers can be used individually or in combination. Certain combinations will often provide a more controlled release of the drug than their components when used individually. Examples include, but are not limited to, the following: a cellulosic polymer combined with a gum, such as hydroxyethylcellulose or hydroxypropylcellulose combined with xanthan gum; a polyalkylene oxide combined with a gum, such as poly(ethylene oxide) combined with xanthan gum; and a polyalkylene oxide combined with a cellulosic polymer, such as poly(ethylene oxide) combined with hydroxyethylcellulose, hydroxypropylcellulose, and/or hydroxypropyl methylcellulose.

Combinations of different poly(ethylene oxide)s are also contemplated, with polymers of different molecular weights contributing to different dosage form characteristics. For example, a very high molecular weight poly(ethylene oxide) such as Polyox® 303 (with a number average molecular weight of 7 million) or Polyox® Coag (with a number average molecular weight of 5 million) may be used to significantly enhance diffusion relative to disintegration release by providing high swelling as well as tablet integrity. Incorporating a lower molecular weight poly(ethylene oxide) such as Polyox® WSR N-60K (number average molecular weight approximately 2 million) with Polyox® 303 and/or Polyox® Coag increases disintegration rate relative to diffusion rate, as the lower molecular weight polymer reduces swelling and acts as an effective tablet disintegrant. Incorporating an even lower molecular weight poly(ethylene oxide) such as Polyox® WSR N-80 (number average molecular weight approximately 200,000) further increases disintegration rate.

The hydrophilicity and water swellability of the polymers used herein cause the drug-containing matrices to swell in size in the gastric cavity due to ingress of water in order to achieve a size that will be retained in the stomach when introduced during the fed mode. These qualities also cause the matrices to become slippery, which provides resistance to peristalsis and further promotes their retention in the stomach. The release rate of a drug from the matrix is primarily dependent upon the rate of water imbibition and the rate at which the drug dissolves and diffuses from the swollen polymer, which in turn is related to the solubility and dissolution rate of the drug, the drug particle size and the drug concentration in the matrix.

The amount of polymer relative to the drug can vary, depending on the drug release rate desired and on the polymer, its molecular weight, and excipients that may be present in the formulation. Preferably, the amount of polymer is effective to provide a desired extended release period within the fed stomach, such that the time to reach maximum plasma concentration ($t_{max}$) is at least one hour longer, preferably at least two hours longer, and most preferably at least three hours longer, than that observed with immediate release dosage forms intended to deliver the same drug. In this way, the required doses per day can be reduced. However, a competing consideration is the desirability of releasing the majority of drug in the stomach and upper G.I. tract, meaning that the amount of polymer should also be effective to release most of or even all the drug before the drug and/or dosage form passes into the lower intestinal tract. Ideally, at least 75 wt. %, preferably at least 85 wt. %, and more preferably at least 90 wt. % of the drug is released to the stomach, duodenum, and upper intestinal tract within two to ten hours, preferably within four to nine hours, more preferably within four to six hours, after ingestion. Both goals here can be easily attained with active agents such as ciprofloxacin that exhibit their therapeutic effect for a time period extending beyond their half-life, meaning that only a modest extension of the drug delivery period is necessary to reduce the number of doses per day, e.g., from a twice-a-day dosing regimen to a once-a-day dosing regimen.

It has now been found that higher molecular weight polymers are preferred to provide a desired extended release profile using the present dosage forms. Suitable molecular weights are generally in the range of about 5,000 to about 20,000,000. For sparingly soluble drugs, the polymers have molecular weights preferably in the range of about 5,000 to about 8,000,000, more preferably in the range of about 10,000 to about 5,000,000. For water-soluble drugs, the polymers preferably have molecular weights of at least about 10,000, but the molecular weight used will vary with the selected polymer. For example, for hydroxypropyl methylcellulose, the minimum molecular weight may be as low as 10,000, while for poly(ethylene oxide)s the molecular weight may be far higher, on the order of 2,000,000 or more.

IV. Active Agents

The dosage forms of the present invention are effective for the continuous, controlled administration of drugs that are capable of acting either locally within the gastrointestinal tract, or systemically by absorption into circulation via the gastrointestinal mucosa. Gastric-retentive dosage forms such as those disclosed and claimed herein are particularly useful for the delivery of drugs that are relatively insoluble, are ionized within the gastrointestinal tract, or require active transport.

Preferred active agents for administration using the present dosage forms are those that have increased aqueous solubility in more acidic media, i.e., those whose aqueous solubility increases with decreasing pH. For example, a relatively hydrophobic basic drug that exists in the form of a free base at about neutral pH but which is ionized at a lower pH could be expected to exhibit the aforementioned solubility profile. The aqueous solubility of the active agent in an acidic environment is not necessarily high; the active agent may in fact be only slightly soluble at low so long as it becomes even less soluble, and preferably substantially insoluble, in water at higher pH. The active agents may be acidic, basic, or in the form of an acid addition salt. Generally, the pH at which the pH at which the drug becomes substantially insoluble is in the range of 5 to 8, generally 5 to 7.5

The active agent administered may be any compound that is suitable for oral drug administration; examples of the various classes of active agents that can be administered using the present dosage forms include, but are not limited to: analgesic agents; anesthetic agents; antiarthritic agents; respiratory drugs; anticancer agents; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antineoplastic agents; antiparkinsonism drugs; antipruritics; antipsychotics; antipyretics; antispasmodics; antitubercular agents; antiulcer agents and other gastrointestinally active agents; antiviral agents; anxiolytics; appetite suppressants; attention deficit disorder (ADD) and attention deficit hyperactivity disorder (ADHD) drugs; cardiovascular preparations including calcium channel blockers, CNS agents, and vasodilators; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nutritional agents, such as vitamins, essential amino acids and fatty acids; parasympatholytics; peptide drugs; psychostimulants; sedatives; steroids; sympathomimetics; and tranquilizers.

Commonly known drugs that are substantially insoluble or only slightly soluble in water include, by way of example, the following:

Gastrointestinally Active Agents.

Gastrointestinally active agents are particularly preferred drugs that can be administered using the present dosage forms. These types of drugs include agents for inhibiting gastric acid secretion, such as the $H_2$ receptor antagonists cimetidine, ranitidine, famotidine, and nizatidine, the $H^+$, $K^+$-ATPase inhibitors (also referred to as "proton pump inhibitors") omeprazole and lansoprazole, and antacids such as calcium carbonate, aluminum hydroxide, and magnesium hydroxide. Also included within this general group are agents for treating infection with *Helicobacter pylori* (*H. pylori*), such as metronidazole, tinidazole, amoxicillin, clarithromycin, tetracycline, thiamphenicol, and bismuth compounds (e.g., bismuth subcitrate and bismuth subsalicylate). Other gastrointestinally active agents administrable using the present dosage forms include, but are not limited to, pentagastrin, carbenoxolone, sulfated polysacseharides such as sucralfate, prostaglandins such as misoprostol, and muscarinic antagonists such as pirenzepine and telenzepine. Additionally included are antidiarrheal agents, antiemetic agents and prokinetic agents such as ondansetron, granisetron, metoclopramide, chlorpromazine, perphenazine, prochlorperazine, promethazine, thiethylperazine, trifluromazine, domperidone, trimethobenzamide, cisapride, motilin, loperamide, diphenoxylate, and octreotide.

Anti-Microbial Agents.

These include: quinolone antibiotics such as nalidixic acid, and particularly fluorinated quinolone antibiotics such as ciprofloxacin, clinafloxacin, enoxacin, gatifloxacin, grepafloxacin, levofloxacin, lomefloxacin, moxifloxacin, norfloxacin, ofloxacin, pefloxacin, sparfloxacin, and trovafloxacin; tetracycline antibiotics and related compounds (chlortetracycline, oxytetracycline, demeclocycline, methacycline, doxycycline, minocycline, rolitetracycline); macrolide antibiotics such as erythromycin, clarithromycin, and azithromycin; streptogramin antibiotics such as quinupristin and dalfopristin; beta-lactam antibiotics, including penicillins (e.g., penicillin G, penicillin VK), antistaphylococcal penicillins (e.g., cloxacillin, dicloxacillin, nafcillin, and oxacillin), extended spectrum penicillins (e.g., aminopenicillins such as ampicillin and amoxicillin, and the antipseudomonal penicillins such as carbenicillin), and cephalosporins (e.g., cefadroxil, cefepime, cephalexin, cefazolin, cefoxitin, cefotetan, cefuroxime, cefotaxime, ceftazidime, and ceftriaxone), and carbapenems such as imipenem, meropenem and aztreonam; aminoglycoside antibiotics such as streptomycin, gentamicin, tobramycin, amikacin, and neomycin; glycopeptide antibiotics such as teicoplanin; sulfonamide antibiotics such as sulfacetamide, sulfabenzamide, sulfadiazine, sulfadoxine, sulfamerazine, sulfamethazine, sulfamethizole, and sulfamethoxazole; anti-mycobacterials such as isoniazid, rifampin, rifabutin, ethambutol, pyrazinamide, ethionamide, aminosalicylic, and cycloserine; systemic antifungal agents such as itraconazole, ketoconazole, fluconazole, and amphotericin B; antiviral agents such as acyclovir, famcicylovir, ganciclovir, idoxuridine, sorivudine, trifluridine, valacyclovir, vidarabine, didanosine, stavudine, zalcitabine, zidovudine, amantadine, interferon alpha, ribavirin and rimantadine; and miscellaneous antimicrobial agents such as chloramphenicol, spectinomycin, polymyxin B (colistin), bacitracin, nitrofurantoin, methenamine mandelate and methenamine hippurate.

Anti-Diabetic Agents.

These include, by way of example, acetohexamide, chlorpropamide, ciglitazone, gliclazide, glipizide, glucagon, glyburide, miglitol, pioglitazone, tolazamide, tolbutamide, triampterine, and troglitazone.

Analgesics.

Non-opioid analgesic agents include apazone, etodolac, difenpiramide, indomethacin, meclofenamate, mefenamic acid, oxaprozin, phenylbutazone, piroxicam, and tolmetin; opioid analgesics include alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil, and tramadol.

Anti-Inflammatory Agents.

Anti-inflammatory agents include the nonsteroidal anti-inflammatory agents, e.g., the propionic acid derivatives as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, and fenbufen; apazone; diclofenac; difenpiramide; diflunisal; etodolac; indomethacin; ketorolac; meclofenamate; nabumetone; phenylbutazone; piroxicam; sulindac; and tolmetin. Steroidal anti-inflammatory agents include hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17, 21-diesters (e.g., hydrocortisone-17,21-diacetate, hydrocortisone-7-acetate-21-butyrate, hydrocortisone-17, 21-dibutyrate, etc.), alclometasone, dexamethasone, flumethasone, prednisolone, and methylprednisolone.

Anti-Convalsant Agents.

Suitable anti-convulsant (anti-seizure) drugs include, by way of example, azetazolamide, carbamazepine, clonazepam, clorazepate, ethosuximide, ethotoin, felbamate, lamotrigine, mephenyloin, mephobarbital, phenyloin, phenobarbital, primidone, trimethadione, vigabatrin, topiramate, and the benzodiazepines. Benzodiazepines, as is well known, are useful for a number of indications, including anxiety, insomnia, and nausea.

CNS and Respiratory Stimulants.

CNS and respiratory stimulants also encompass a number of active agents. These stimulants include, but are not limited to, the following: xanthines such as caffeine and theophylline; amphetamines such as amphetamine, benzphetamine hydrochloride, dextroamphetamine, dextroamphetamine sulfate, levamphetamine, levamphetamine hydrochloride, methamphetamine, and methamphetamine hydrochloride; and miscellaneous stimulants such as methylphenidate, methylphenidate hydrochloride, modafinil, pemoline, sibutramine, and sibutramine hydrochloride.

Neuroleptic Agents.

Neuroleptic drugs include antidepressant drugs, antimanic drugs, and antipsychotic agents, wherein antidepressant drugs include (a) the tricyclic antidepressants such as amoxapine, amitriptyline, clomipramine, desipramine, doxepin, imipramine, maprotiline, nortriptyline, protriptyline, and trimipramine, (b) the serotonin reuptake inhibitors citalopram, fluoxetine, fluvoxamine, paroxetine, sertraline, and venlafaxine, (c) monoamine oxidase inhibitors such as phenelzine, tranylcypromine, and (−)-selegiline, and (d) other, "atypical" antidepressants such as nefazodone, trazodone and venlafaxine, and wherein antimanic and antipsychotic agents include (a) phenothiazines such as acetophenazine, acetophenazine maleate, chlorpromazine, chlorpromazine hydrochloride, fluphenazine, fluphenazine hydrochloride, fluphenazine enanthate, fluphenazine decanoate, mesoridazine, mesoridazine besylate, perphenazine, thioridazine, thioridazine hydrochloride, trifluoperazine, and trifluoperazine hydrochloride, (b) thioxanthenes such as chlorprothixene, thiothixene, and thiothixene hydrochloride, and (c) other heterocyclic drugs such as carbamazepine, clozapine, droperidol, haloperidol, haloperidol decanoate, loxapine succinate, molindone, molindone hydrochloride, olanzapine, pimozide, quetiapine, risperidone, and sertindole.

Hypnotic agents and sedatives include clomethiazole, ethinamate, etomidate, glutethimide, meprobamate, methyprylon, zolpidem, and barbiturates (e.g., amobarbital, aprobarbital, butabarbital, butalbital, mephobarbital, methohexital, pentobarbital, phenobarbital, secobarbital, thiopental).

Anxiolytics and tranquilizers include benzodiazepines (e.g., alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, triazolam), buspirone, chlordiazepoxide, and droperidol.

Anticancer Agents, Including Antineoplastic Agents:

Paclitaxel, docetaxel, camptothecin and its analogues and derivatives (e.g., 9-aminocamptothecin, 9-nitrocamptothecin, 10-hydroxy-camptothecin, irinotecan, topotecan, 20-O-β-glucopyranosyl camptothecin), taxanes (baccatins, cephalomannine and their derivatives), carboplatin, cisplatin, interferon-$\alpha_{2A}$, interferon-$\alpha_{2B}$, interferon-$\alpha_{N3}$ and other agents of the interferon famil5', levamisole, altretamine, cladribine, tretinoin, procarbazine, dacarbazine, gemcitabine, mitotane, asparaginase, porfimer, mesna, amifostine, mitotic inhibitors including podophyllotoxin derivatives such as teniposide and etoposide and ymca alkaloids such as vinorelbine, vincristine and vinblastine.

Antihyperlipidemic Agents.

Lipid-lowering agents, or "hyperlipidemic" agents," include HMG-CoA reductase inhibitors such as atorvastatin, simvastatin, pravastatin, lovastatin and cerivastatin, and other lipid-lowering agents such as clofibrate, fenofibrate, gemfibrozil and tacrine.

Anti-Hypertensive Agents.

These include amlodipine, benazepril, darodipine, dilitazem, diazoxide, doxazosin, enalapril, eposartan, losartan, valsartan, felodipine, fenoldopam, fosinopril, guanabenz, guanadrel, guanethidine, guanfacine, hydralazine, metyrosine, minoxidil, nicardipine, nifedipine, nisoldipine, phenoxybenzamine, prazosin, quinapril, reserpine, and terazosin.

Cardiovascular Preparations.

Cardiovascular preparations include, by way of example, angiotensin converting enzyme (ACE) inhibitors such as enalapril, 1-carboxymethyl-3-1-carboxy-3-phenyl-(1S)-propylamino-2,3,4,5-tetrahydro-1H-(3S)-1-benzazepine-2-one, 3-(5-amino-1-carboxy-1S-pentyl)amino-2,3,4,5-tetrahydro-2-oxo-3S-1H-1-benzazepine-1-acetic acid or 3-(1-ethoxycarbonyl-3-phenyl-(1S)-propylamino)-2,3,4,5-tetrahydro-2-oxo-(3S)-benzazepine-1-acetic acid monohydrochloride; cardiac glycosides such as digoxin and digitoxin; inotropes such as amrinone and milrinone; calcium channel blockers such as verapamil, nifedipine, nicardipene, felodipine, isradipine, nimodipine, bepridil, amlodipine and diltiazem; beta-blockers such as atenolol, metoprolol; pindolol, propafenone, propranolol, esmolol, sotalol, timolol, and acebutolol; antiarrhythmics such as moricizine, ibutilide, procainamide, quinidine, disopyramide, lidocaine, phenytoin, tocainide, mexiletine, flecainide, encainide, bretylium and amiodarone; and cardioprotective agents such as dexrazoxane and leucovorin; and vasodilators such as nitroglycerin; and diuretic agents such as hydrochlorothiazide, furosemide, bumetanide, ethacrynic acid, torsemide, azosemide, muzolimine, piretanide, and tripamide.

Anti-Viral Agents.

Antiviral agents that can be delivered using the present dosage forms include the antiherpes agents acyclovir, famciclovir, foscamet, ganciclovir, idoxuridine, sorivudine, trifluridine, valacyclovir, and vidarabine; the antiretroviral agents didanosine, stavudine, zalcitabine, and zidovudine; and other antiviral agents such as amantadine, interferon alpha, ribavirin and rimantadine.

Sex Steroids.

The sex steroids include, first of all, progestogens such as acetoxypregnenolone, allylestrenol, anagestone acetate, chlormadinone acetate, cyproterone, cyproterorie acetate, desogestrel, dihydrogesterone, dimethisterone, ethisterone (17α-ethinyltestosterone), ethynodiol diacetate, fluorogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norg- estrienone, normethisterone, and progesterone. Also included within this general class are estrogens, e.g.: estradiol (i.e., 1,3,5-estratriene-3,17β-diol, or "17β-estradiol") and its esters, including estradiol benzoate, valerate, cypionate, heptanoate, decanoate, acetate and diacetate; 17α-estradiol; ethinylestradiol (i.e., 17α-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Androgenic agents, also included within the general class of sex steroids, are drugs such as the naturally occurring androgens androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA; also termed "prasterone"), sodium dehydroepiandrosterone sulfate, 4-dihydrotestosterone (DHT; also termed "stanolone"), 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone such as methyl testosterone, testolactone, oxymetholone and fluoxymesterone.

Muscarinic Receptor Agonists and Antagonists.

Muscarinic receptor agonists include, by way of example: choline esters such as acetylcholine, methacholine, carbachol, bethanechol (carbamylmethylcholine), bethanechol chloride, cholinomimetic natural alkaloids and synthetic analogs thereof, including pilocarpine, muscarine, McN-A-343, and oxotremorine. Muscarinic receptor antagonists are generally belladonna alkaloids or semisynthetic or synthetic analogs thereof, such as atropine, scopolamine, homatropine, homatropine methyl bromide, ipratropium, methantheline, methscopolamine and tiotropium.

Peptide Drugs.

Peptidyl drugs include the peptidyl hormones activin, amylin, angiotensin, atrial natriuretic peptide (ANP), calcitonin, calcitonin gene-related peptide, calcitonin N-terminal flanking peptide, ciliary neurotrophic factor (CNTF), corticotropin (adrenocorticotropin hormone, ACTH), corticotropin-releasing factor (CRF or CRH), epidermal growth factor (EUF), follicle-stimulating hormone (FSH), gastrin, gastrin inhibitory peptide (alP), gastrin-releasing peptide, gonadotropin-releasing factor (GnRF or GNRH), growth hormone releasing factor (GRF, GRH), human chorionic gonadotropin (hCH), inhibin A, inhibin B, luteinizing hormone (LH), luteinizing hormone-releasing hormone (LHRH), a-melanocyte-stimulating hormone, $3-melanocyte-stimulating hormone, y-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatotropin (growth hormone, GH), somatostatin (SW, growth hormone-release inhibiting factor. GIF), thyrotropin (thyroid-stimulating, hormone, TSH), thyrotropin-releasing factor (TRH or TRF), thyroxine, vasoactive intestinal peptide (VIP), and vasopressin. Other peptidyl drugs are the cytokines, e.g., colony stimulating factor 4. heparin binding neurotrophic factor (HBNF), interferon-α, interferon α-2a, interferon α-2b. interferon α-n3, interferon-β, etc., interleukin-1, interleukin-2, interleukin-3, interleukin-4, interleukin-5, interleukin-6, etc., tumor necrosis factor, tumor necrosis factor-ct, granuioyote colony-stimulating factor (G-CSF), granulocytemacrophage colony-stimulating factor (GM-CSF), macrophage colony-stimulating factor, midkine (MD), and thymopoietin. Still other peptidyl drugs that can be advantageously delivered using the present systems include endorphins (e.g., dermorphin, dynorphin, α-endorphin, β-endorphin, γ-endorphin, σ-endorphin, [Leu$^5$]enkephalin, [Met$^5$]enkephalin, substance P), kinins (e.g., bradykinin, potentiator B, bradykinin potentiator C, LHRH analogues (e.g., buserelin, deslorelin, fertirelin, goserelin, histrelin, leuprolide, lutrelin, nafarelin, tryptorelin), and the coagulation factors, such as $α_1$-antitrypsin, $α_2$-macroglobulin, antithrombin III, factor I (fibrinogen), factor II (prothrombin), factor III (tissue prothrombin), factor V (proaccelerin), factor VII (proconvertin), factor VIII (antihemophilic globulin or AHG), factor IX (Christmas factor, plasma thromboplastin component or PTC), factor X (Stuart-Power factor), factor XI (plasma thromboplastin antecedent or PTA), factor XII (Hageman factor), heparin cofactor II, kallikrein, plasmin, plasminogen, prekallikrein, protein C, protein S, and thrombomodulin and combinations thereof.

Genetic material may also be delivered using the present dosage forms, e.g., nucleic acids, RNA, DNA, recombinant RNA, recombinant DNA, antisense RNA, antisense DNA, ribozymes, ribooligonucleotides, deoxyribonucleotides, antisense ribooligonucleotides, and antisense deoxyribooligonucleotides. Representative genes include those encoding, far vascular endothelial growth factor, fibroblast growth factor, Bcl-2, cystic fibrosis transmembrane regulator, nerve growth factor, human growth factor, erythropoietin, tumor necrosis factor, and interleukin-2, as well as histocompatibility genes such as HLA-B7.

In contrast to many erodible dosage forms, the low variability of the present dosage forms is particularly important for poorly soluble drugs such as phenyloin and carbamazepine, both anticonvulsant drugs used in the treatment of epilepsy, as noted above, and for which, due to wide variation in drug absorption from patient to patient, doctors must now titrate their patients individually to find a proper (i.e., and effective) dosage regimen. In this regard, the dosage forms of the invention are useful for more consistent delivery of sparingly soluble drugs that have a narrow therapeutic index, i.e., drugs for which the toxic dose is not significantly higher than the effective dose.

The dosage forms of the present invention are particularly useful for delivering drugs directly into the stomach for an extended period of time, for example, when the drug is preferentially absorbed in the small intestine (e.g., ciprofloxacin), or for providing continuous, local-only (non-systemic) action, for example, when the drug is calcium carbonate, and which when incorporated into the dosage forms of the present invention becomes a non-systemic, controlled-release antacid. The dosage forms are also useful for delivering drugs continuously to the stomach that are only soluble in that portion of the gastrointestinal tract. For instance, the dosage forms of the present invention are useful for the delivery of calcium carbonate or other calcium salts intended to be used as an antacid or as a dietary supplement to prevent osteoporosis. Calcium salts are soluble in the stomach but not in the remainder of the G.I. tract, as a result of the presence of stomach acid. With conventional dosage forms, the dwell time of the delivered agent in the stomach is limited usually to only about 20 to 40 minutes, which, in turn, results in a calcium availability of only about 15 to 30%. As a consequence, extremely large dosage forms (2.5 grams), which are difficult for patients to swallow, are commonly utilized. In contrast, by providing controlled delivery for about 4 to 9 hours, plus gastric retention of from about 2 to 12, preferably 4 to 9 hours, most preferably about 4 to 6 hours, the dosage forms of the present invention assure more complete bioavailability of elemental calcium from the administered drug, i.e., calcium carbonate. This results in a greater likelihood of patients receiving the intended dose and, also, avoids the need for impractically large dosage forms.

The dosage forms of the present invention are also useful for delivering drugs to treat local disorders of the stomach, such as those that are effective for eradicating *Helicobacter pylori* (*H. pylori*) from the submucosal tissue of the stomach, to treat stomach and duodenal ulcers, to treat gastritis and esophagitis and to reduce risk of gastric carcinoma. The dosage forms of the present invention are particularly useful for the foregoing indications because they provide enhanced gastric retention and prolonged release. In a preferred such embodiment, a dosage form of the invention will comprise a combination of (a) bismuth (e.g., as bismuth subsalicylate), (b) an antibiotic such as tetracycline, amoxicillin, thiamphenicol, or clarithromycin, and (c) a proton pump inhibitor, such as omeprazole. A combination of bismuth subsalicylate, thiamphenicol and omeprazole is a particularly preferred combination that may be delivered using the dosage forms of the present invention for the eradication of *H. pylori*.

Drugs delivered from the gastric-retentive, controlled delivery dosage forms of the invention continuously bathe the stomach and upper part of the small intestine—in particular, the duodenum—for many hours. These sites, particularly the upper region of the small intestine, are the sites of most efficient absorption for many drugs. By continually supplying the drug to its most efficient site of absorption, the dosage forms of the present invention allow for more effective oral use of many drugs.

Since the dosage forms of the present invention provide the drug by means of a continuous delivery instead of the pulse-entry delivery associated with conventional dosage forms, two particularly significant benefits result from their use: (1) a reduction in side effects from the drug(s); and (2) an ability to effect treatment with less frequent administration of the drug(s) being used. For instance, when administered in a conventional dosage form, the sparingly soluble drug, ciprofloxacin, an antibiotic administered to treat bacterial infections such as urinary tract infections, is currently given two times daily and may be frequently accompanied by gastrointestinal side effects such as diarrhea. However, using the dosage forms of the present invention, the number of daily doses can be decreased to one with a lower incidence of side effects.

The invention is not, however, limited to dosage forms for delivering poorly soluble drugs. Drugs having moderate to substantial aqueous solubility can also be delivered using the present dosage forms. If necessary, they may be encased in a protective vesicle or coated with a protective coating so as to prevent a too rapid release. Preferred such drugs include, without limitation, metformin hydrochloride, vancomycin hydrochloride, captopril, enalopril or its salts, erythromycin lactobionate, ranitidine hydrochloride, sertraline hydrochloride, ticlopidine hydrochloride, amoxicillin, cefuroxime axetil, cefaclor, clindamycin, doxifluridine, gabapentin, tramadol, fluoxetine hydrochloride, acyclovir, levodopa, ganciclovir, bupropion, lisinopril, losartan, and esters of ampicillin. Particularly preferred such drugs are metformin hydrochloride, gabapentin, lisinopril, enalopril, losartan, and sertraline hydrochloride.

Any of the aforementioned active agents may also be administered in combination using the present dosage thrifts. Examples of particularly important drug combination products include, but are not limited to, an ACE inhibitor or an angiotensin II antagonist in combination with a diuretic. Specific examples of ACE inhibitors are captopril, lisinopril, or enalopril, and examples of diuretics include triampterine, furosemide, bumetanide, and hydrochlorothiazide. Alternatively, either of these diuretics can advantageously be used in combination with a beta-adrenergic blocking agent such as propranolol, timolol or metoprolol. These particular combinations are useful in cardiovascular medicine, and provide advantages of reduced cost over separate administrations of the different drugs, plus the particular advantage of reduced side effects and enhanced patient compliance. For example, it has been shown that small doses of a diuretic plus small doses of either an ACE inhibitor or a beta blocker provide the additive effects of lowering blood pressure without the additive side effects of the two together.

Particularly preferred drugs for administration using the present dosage forms include, but are not limited to, furosemide, gabapentin, losartan, budesonide, and the antibiotics ciprofloxacin and minocycline. The drugs may be in the form of salts, esters or other derivatives. For example, ciprofloxacin and minocycline may be incorporated as acid addition salts, such as ciprofloxacin hydrochloride and minocy~line hydrochloride, respectively.

Drug loading may be expressed in terms of the volume fraction of drug relative to the entire dosage form, or, if the dosage form is a bilayer or trilayer tablet, in terms of the volume fraction of drug relative to the erodible layer in which it is contained. The drug loading in the present dosage forms is in the range of about 0.01% to 80%, but is preferably relatively high, i.e., at least about 60%, preferably in the range of about 60% to 80%, such that the rate of erosion is essentially drug-controlled.

V. Dosage Forms, Protective Vesicles and Coatings

The formulations of this invention are typically in the form of matrix/active agent tablets, or matrix/active agent particles compressed into tablets. Other formulations contain matrix/active agent particles in capsules. The encapsulating material should be highly soluble so that the particles are freed and rapidly dispersed in the stomach after the capsule is ingested. Such dosage forms are prepared using conventional methods known to those in the field of pharmaceutical formulation and described in the pertinent texts, e.g., in *Remington*, cited supra. Tablets and capsules represent the most convenient oral dosage forms, in which cases solid pharmaceutical carriers are employed.

Tablets may be manufactured using standard tablet processing procedures and equipment. One method for forming tablets is by direct compression of a particulate composition, with the individual particles of the composition comprised of a matrix of a biocompatible, hydrophilic, erodible polymer having the active agent incorporated therein, alone or in combination with one or more carriers, additives, or the like. As an alternative to direct compression, tablets can be prepared using wet-granulation or dry-granulation processes. Tablets may also be molded rather than compressed, starting with a moist or otherwise tractable material, and using injection or compression molding techniques using suitable molds fitted to a compression unit. Tablets may also be prepared by extrusion in the form of a paste, into a mold, or to provide an extrudate to be "cut" into tablets. However, compression and granulation techniques are preferred, with direct compression particularly preferred.

Tablets prepared for oral administration according to the invention, and manufactured using direct compression, will generally contain other materials such as binders, lubricants, disintegrants, fillers, stabilizers, solubilizers, emulsifiers, surfactants, complexing agents, coloring agents, and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate (in a concentration of from 0.25% to 3% by weight, preferably from about 1.5% to 2.5% by weight), calcium stearate, stearic acid, and hydrogenated vegetable oil (preferably comprised of hydrogenated and refined triglycerides of stearic and palmitic acids at about 1% to 5% by weight, most preferably less than about 2% by weight). Disintegrants are used to facilitate disintegration of the tablet, thereby increasing the erosion rate relative to the dissolution rate, and are generally starches, clays, celluloses, algins, gums, or crosslinked polymers (e.g., crosslinked polyvinyl pyrrolidone). Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Solubility-enhancers, including solubilizers per se, emulsifiers, and complexing agents (e.g., cyclodextrins), may also be advantageously included in the present formulations. Stabilizers, as well known in the art, are used to inhibit or retard drug decomposition reactions that include, by way of example, oxidative reactions.

As noted above, the active agent/polymer matrix particles of the invention may also be administered in packed capsules. Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy*, cited supra, which describes materials and methods for preparing encapsulated pharmaceuticals.

As previously mentioned, the dosage forms of the present invention can additionally be used to deliver a drug incorporated into a protective vesicle and/or coated with a protective coating. That is, as explained in U.S. Pat. No. 5,972,389 to Shell et al., cited supra, water-soluble drugs can be rendered substantially insoluble or only slightly soluble when incorporated into protective vesicles and/or coated with a protective coating. Suitable vesicles include, but are not limited to, liposomes and nanoparticles, e.g., nanospheres, nanocapsules and nanocrystals composed of amino acids. Vesicles may also be used to solubilize drugs that otherwise have limited aqueous solubility.

By incorporating a drug either in a protective vesicle or protective coating into the dosage form of the present invention, the benefits of gastric retention and gradual release to the upper 0.1. tract are combined with the advantageous properties of the vesicle or coating. Advantageous properties associated with the use of protective vesicles and coatings include, for example, enhancing drug absorption and/or altering drug solubility. In this context, the drug in combination with either agent is continuously and gradually released from the gastric-retentive system to bathe the duodenum and the remainder of the small intestine in a prolonged manner which is determined by the rate at which the polymer erodes.

Examples of such vesicles include liposomes, which can protect an incorporated drug from the time it leaves the dosage form until it reaches the absorption site. Methods for preparing liposome encapsulated drug systems are known to and used by those of skill in the art. A general discussion, which includes an extensive bibliography regarding liposomes and methods for their preparation, can be found in "*Liposomes, A Practical Approach*," R.R.C New, Ed., 1990. Further examples of suitable vesicles include microparticulate systems, which are exemplified by nanoparticles and proteinoid and amino acid microspheres and pharmacosomes. Nanoparticles include, for example, nanospheres, nanocapsules, and nanocrystals. The matrix-like structure of the nanosphere allows the drug to be contained either within the matrix or coated on the outside. Nanoparticles may also consist of stabilized submicron structures of drug with or without surfactant or polymeric additives. Nanocapsules have a shell of polymeric material and, as with the nanospheres, the drug can be contained either within the shell or coated on the outside. Polymers that can be used to prepare the nanoparticles include, but are not limited to, polyacrylamide, poly(alkyl methacrylates), poly(alkyl cyanoacrylates), polyglutaraldehyde, poly(lactide-co-glycolide) and albumin. For details pertaining to nanoparticle preparation, see, e.g., Allemann, E., et al., "Drug-Loaded Nanoparticles-Preparation Methods and Drug Targeting Issues," *Eur. J. Pharm. Biopharm.* 39(5):173-191, 193.

The dosage forms of the invention may also be formulated as bilayer tablets, trilayer tablets, or shell-and-core tablets, with bilayer and tri layer tablets preferred. In any of these embodiments wherein a dosage form is composed of two or more discrete regions each with different functions or attributes (e.g., a bilayer tablet with one layer being primarily swellable, and the other layer being primarily erodible), two or more drugs can be delivered in two or more different regions (e.g., layers), where the polymer or polymers in each region are tailored to provide a dissolution, erosion and/or release profile, taking the solubility and molecular weight of the drug into account. For example, a bilayer tablet may be prepared with one drug incorporated into an erosional layer and a second drug, which may or may not be identical to the first drug, incorporated into a swelling layer, or a single drug may be incorporated into an erosional layer, with no active agent in the swelling layer. As another example, a trilayer tablet may be prepared with a two outer layers containing drug, comprised of a polymer that is primarily erodible, with a swellable intermediate layer therebetween. The function of the swelling layer is to provide sufficient particle size throughout the entire period of drug delivery to promote gastric retention in the fed mode. In other embodiments, a drug may be included in a coating for immediate release.

VI. Dosage and Administration

Different drugs have different biological half-lives, which determine their required frequency of administration (once daily, four times daily, etc.). Thus, when two or more drugs are co-administered in one conventional medication unit, an unfavorable compromise is often required, resulting in an underdose of one drug and an overdose of the other. One of the advantages of the dosage forms of the present invention is that they can be used to deliver multiple drugs without requiring such compromises. For example, in an alternative embodiment, a plurality of drug-containing, spherical, spheroidal- or cylindrical-shaped particles are provided, some of the particles containing a first drug/polymer composition designed to release the first drug at its ideal rate and duration (dose), while other particles contain a second drug/polymer composition designed to release the second drug at its ideal rate and duration. In this embodiment, the polymers or polymer molecular weight values used for each of the drugs can be the same or different. Control of the release rate of the differing drugs can also be obtained by combining different numbers of each of the drug/polymer particles in a common dosage form such as a capsule. For example, where two drugs are combined in a capsule made from five particles, three particles would contain one drug and the other two particles would contain the other drug.

Furthermore, the invention provides dosage forms of separate particles, each comprising polymers that may erode at different rates. As a result, the dosage forms of the present invention achieve a plurality of drug delivery rates. For example, the dosage form may comprise three particles, the first and second containing a swellable polymer that erodes and delivers drug over a period of 4 hours, and the third containing a swellable polymer that erodes and delivers drug over a period of 8 hours. In this regard, requisite erosion rates can be achieved by combining polymers of differing erosion rates into a single particle.

In addition, the invention provides dosage forms of separate particles, some comprising polymers that swell, but do not erode and some comprising polymers that swell and erode (with either the same or differing erosion rates). As a result, the dosage forms can achieve a plurality of delivery rates. For example, the dosage form may comprise three particles, the first containing a swellable polymer that delivers drug over a period of 8 hours, the second containing a swellable/erodible polymer that erodes and delivers drug over a period of 4 hours, and the third containing a swellable/erodible polymer that erodes and delivers drug over a period of 6 hours. In this example, the dosage form may contain one, two or three different drugs.

Drugs that are otherwise chemically incompatible when formulated together can be delivered simultaneously via separate swellable particles contained in a single dosage form. For example, the incompatibility of aspirin and prednisolone can be overcome with a dosage form comprising a first swellable particle with one drug and a second swellable particle with the other. In this manner, the gastric retention and simultaneous delivery of a great number of different drugs is now possible.

The dose of drugs from conventional medication forms is specified in terms of drug concentration and administration frequency. In contrast, because the dosage forms of the present invention deliver a drug by continuous, controlled release, a dose of medication used in the disclosed systems is specified by drug release rate and by duration of release. The continuous, controlled delivery feature of the system allows for (a) a reduction in drug side effects, since only the level needed is provided to the patient, and (b) a reduction in the number of doses per day.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

Example 1

Drug dosage forms containing ciprofloxacin hydrochloride were prepared in the form of compressed tablets comprised of swellable, erodible matrix particles with the active agent therein. The matrix particles in the tablets were formulated so as to contain, in a 950 mg tablet, 582 mg ciprofloxacin hydrochloride (equivalent to 500 mg ciprofloxacin), at least one poly(ethylene oxide) (number average molecular weight indicated below), magnesium stearate or stearic acid as a lubricant, and optionally a poly(vinylpyrrolidone) (PVP) hinder. The formulation of each dosage form was as follows:

Formulation GR-1 (caplet, 8.75×635×19.09 mm):
61.35 wt. % ciprofloxacin HCl
14.78 wt % Polyox® WSR N-60K
21.87 wt. % Polyox® WSR N-80
2 wt. % stearic acid Formulation GR-2 (caplet, 8.75×6.43×19.09 mm):
61.35 wt. % ciprofloxacin HCl
36.65 wt. % Polyox® WSR N-60K
2 wt. % stearic acid Formulation GR-3 (oval tablet, 10.05×7.15×18.05 mm):
61.66 wt. % ciprofloxacin HCl
34.43 wt. % Polyox® WSR, N-60K
1.9 wt. % poly(vinyl pyrrolidone) (PVP)
2 wt. % magnesium stearate Immediate Release (IR) Formulation (caplet, 8.75×6.35×19.09 mm):
500 mg ciprofloxacin tablet (Cipro®), obtained from Bayer Corporation The first two formulations were chosen based on the disintegration profile with the expectation that one of the formulations would be retained and deliver ciprofloxacin in the stomach for approximately four hours. These two formulations, as well as the immediate release tablet, were caplet shaped. The third formulation was in the shape of an oval instead of a caplet. The granulation for the oval formulation utilized a PVP binder solution, instead of a Polyox® WSR N-60K binder.

The in vitro release profiles of the dosage forms were evaluated using a USP Dissolution Test and a USP Disintegration Test. Specifically, each dosage form was individually tested in a USP Dissolution Apparatus II using the USP Dissolution Test described in USP 24-NF 19, Supplement 4, Section 711, using 900 mL of deionized water in a 1-liter vessel, anti-evaporation covers, a paddle speed of 100 rpm, and, for purposes of comparison, a paddle speed of 30 rpm. The disintegration test was carried out in a USP Disintegration Apparatus (55-mm stroke at 30 strokes/mm) with fluted disks in place. In vivo pharmacokinetic properties were determined by administering one tablet to each of three human subjects within 5 minutes after consumption of a 350-calorie, high fat standardized meal. Ciprofloxacin absorption was measured by urinary excretion sampled at time intervals of 0, 1, 2, 4, 6, 8, 10, 12 hours and all urine voids up to 48 hours after dosing, collected in 12-hour intervals. Approximately 3 hours later, the subjects consumed a standardized lunch.

Figure 2:
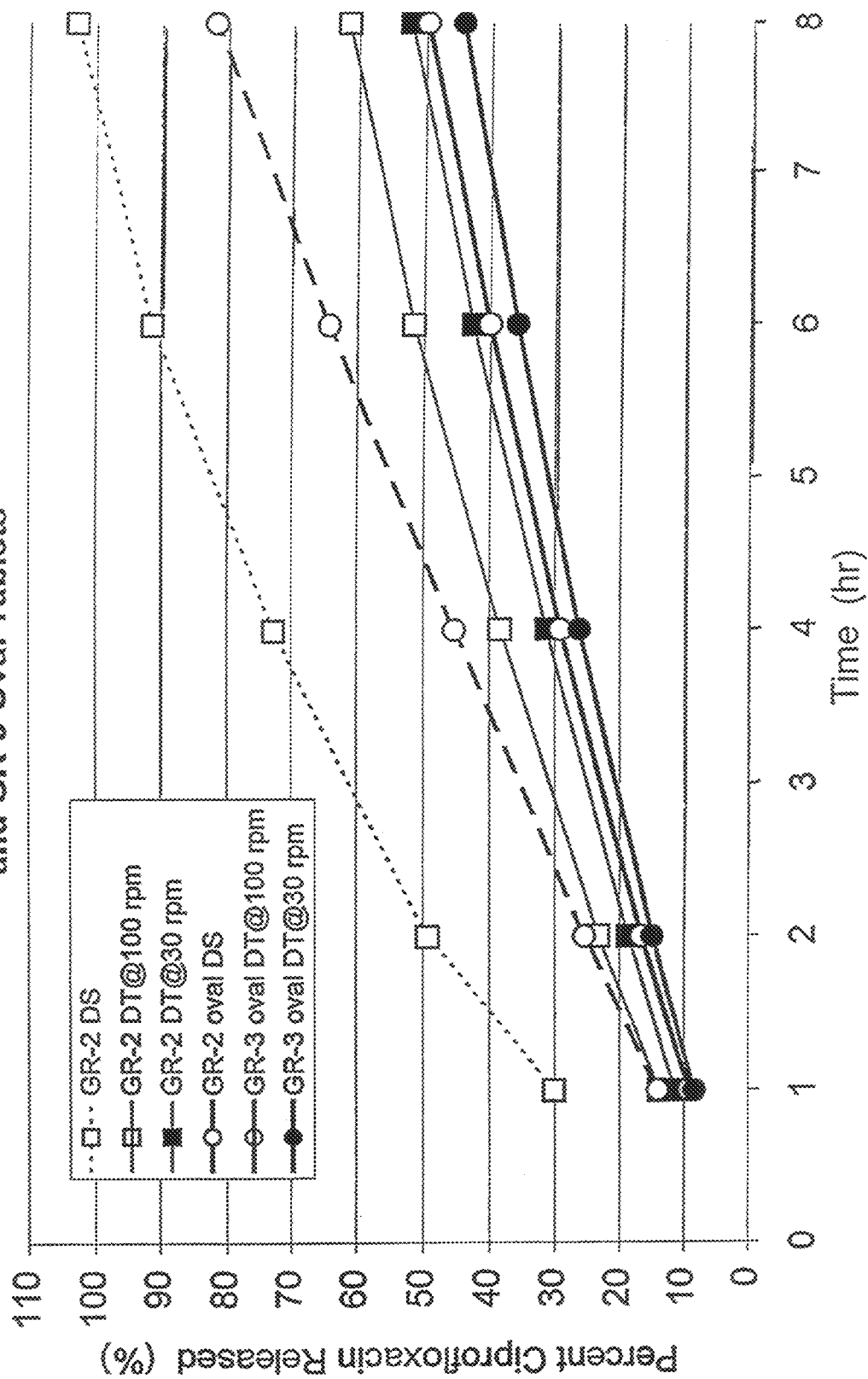

Table 1 and FIGS. 1 and 2 summarize the in vitro release characteristics of the four dosage forms.

TABLE 1

In Vitro Release Characteristics

| FORMULATION | RELEASE BY DISSOLUTION (% DRUG RELEASED @ X HOURS) | RELEASE BY DISINTEGRATION (TIME FOR 90% OF THE DOSAGE FORM TO DISINTEGRATE, "$T_{90}$" IN HOURS) |
|---|---|---|
| GR-1 | 78% @ 8 hrs | 3.3 |
| GR-2 | 62% @ 8 hrs | 5.9 |
| GR-3 | 50% @ 8 hrs | 82% released @ 8 hrs |
| IR (Cipro ®) | 12 minutes | 3 minutes |

Table 2 summarizes the maximum urinary excretion rate of ciprofloxacin from the subjects in the in vivo tests. In general, the maximum urinary excretion rate was lower for all GR dosage forms in comparison with the immediate release tablet, and in fact decreased with increasing in vitro release profile. On the other hand, the $t_{max}$ for the GR dosage forms was more than double that of the immediate release dosage form, indicative of an in vivo extended release profile.

TABLE 2

Summary of Individual Results

| | IR TABLET | | GR-1 | | GR-2 | | GR-3 | |
|---|---|---|---|---|---|---|---|---|
| SUBJECT | Max. Urinary Excretion (mg/hr) | $t_{max}$ (hrs) | Max. Urinary Excretion (mg/hr) | $t_{max}$ (hrs) | Max. Urinary Excretion (mg/hr) | $t_{max}$ (hrs) | Max. Urinary Excretion (mg/hr) | $t_{max}$ (hrs) |
| 1 | 37.4 | 3.0 | 42.3 | 3.0 | 28.4 | 3.0 | 13.7 | 3.0 |
| 2 | 33.2 | 1.5 | 25.4 | 5.0 | 21.5 | 9.0 | 13.2 | 6.5 |
| 3 | 36.0 | 1.5 | 24.6 | 9.0 | 19.3 | 9.0 | 19.5 | 10 |
| Average | 35.5 ± 2.1 | 2.0 | 30.8 ± 10.0 | 5.7 | 23.1 ± 4.7 | 7.0 | 15.5 ± 6.5 | 6.5 |

The average relative bioavailability for the four dosage forms is shown in Table 3. The dose of the immediate release tablet was measured to be 519 mg ciprofloxacin per tablet, instead of the labeled 500 mg. With this taken into account, the relative bioavailability of the GR-1 and GR-2 caplets was equivalent to that of the immediate release tablet.

TABLE 3

| | Summary of Bioavailability and $t_{max}$ Results | | | |
|---|---|---|---|---|
| Subject | IR Tablet | GR-1 | GR-2 | GR-3 |
| Relative Bioavailability | 39.70 ± 0.05% | 39.29 ± 0.06% | 37.40 ± 0.05% | 21.30 ± 0.09% |
| $t_{max}$ | 2.0 ± 0.9 hrs | 5.7 ± 3.1 hrs | 7.0 ± 3.5 hrs | 6.5 ± 3.5 hrs |

Figure 3:
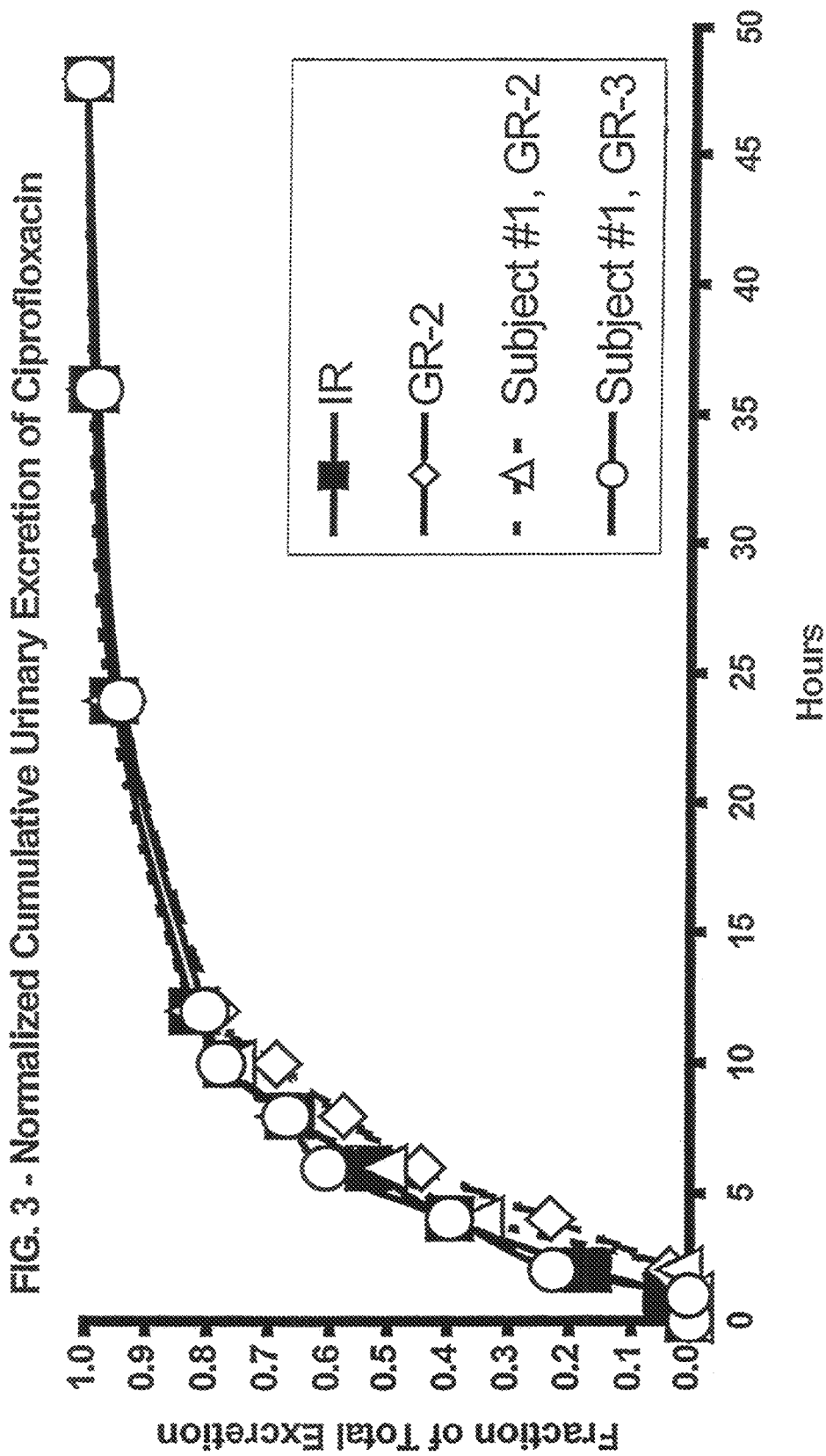
FIGS. 3 and 4 are plots showing the difference in absorption in vivo between the four dosage forms evaluated in Example 1.
Figure 4:
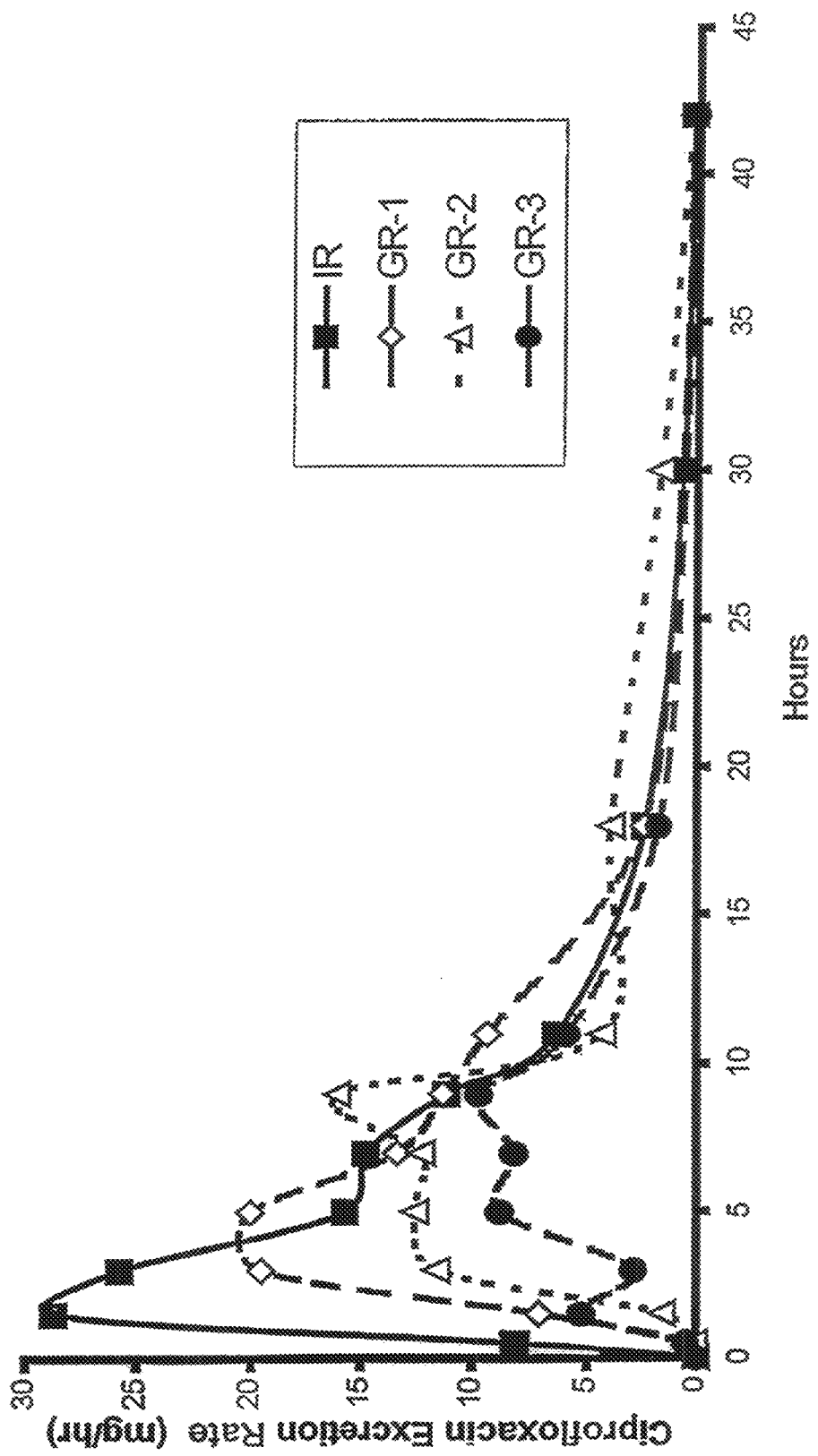

FIGS. 3 and 4 show the difference in absorption from the four dosage forms the three subjects. As may be seen, the GR dosage forms did exhibit extended release profiles, and the AUC's were generally comparable to the IR tablet.

Example 2

The results of the above in vivo study indicated that the release profile of the GR dosage form should be optimized to take advantage of the average gastric residence time. The individual results from the three subjects showed a high degree of variability, due in part to the variability in the rate of drug release from the tablet (i.e., the difference between the disintegration and dissolution release profiles). In order to minimize patient-to-patient variability, formulations were modified so that the in vitro release profile obtained using a disintegration test would approximate the dissolution release profile.

Figure 5:
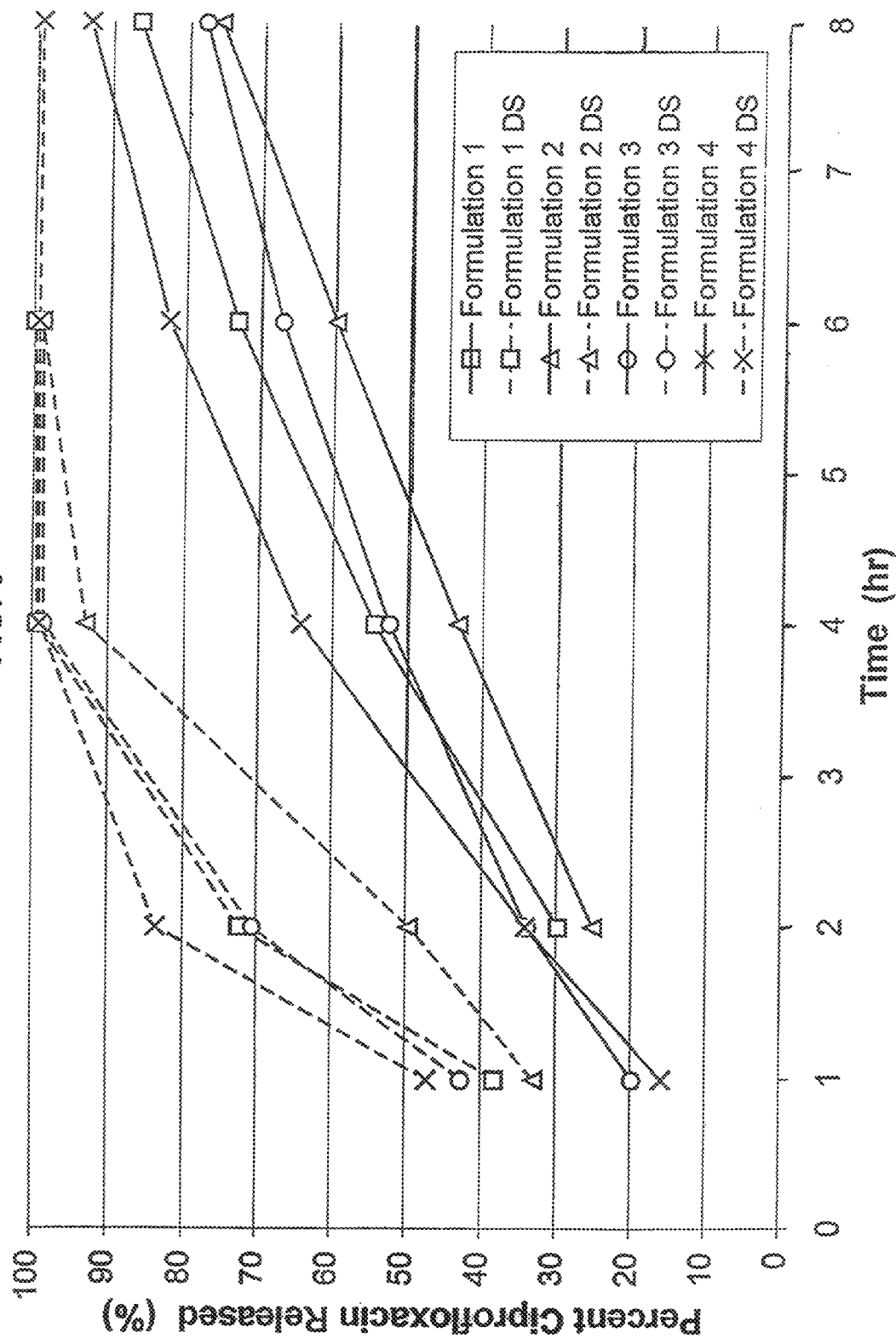
FIG. 5 is a plot showing the release curves obtained from a single layer matrix formulation, using both a disintegration test and a dissolution test, as described in Example 2.

The evaluation procedures were the same as those described above, and the formulations together with the symbols used in FIG. 5 where the results are plotted, were as follows:

Squares, solid line: Dissolution test results for 81.62 wt. % ciprofloxacin HCl,
  13.86 wt. % Polyox® WSR N-60K, 2.52 wt. % PVP, 2.0 wt. % magnesium stearate.
  Tablet dimensions of 10.03×5.94×16.09 mm, tablet weight of 666 mg (containing 544 mg ciprofloxacin HCl), N=6.
Squares, dashed line: Disintegration test results for 81.62 wt. % ciprofloxacin HCl,
  13.86 wt. % Polyox® WSR N-60K, 2.52 wt. % PVP, 2.0 wt. % magnesium stearate.
  Tablet dimensions of 10.03×5.94×16.09 mm, tablet weight of 666 mg (containing 544 mg ciprofloxacin HCl), N=6.
Triangle, solid line: Dissolution test results for 69.38 wt. % ciprofloxacin HCl,
  11.78 wt. % Polyox® WSR N-60K, 15% microcrystalline cellulose (MCC), 2.14 wt. % PVP, 1.7 wt. % magnesium stearate.
  Tablet dimensions of 0.03×5.76×16.06 mm, tablet weight of 800 mg (containing 555 mg ciprofloxacin HCl), N=6.
Triangle, dashed line: Disintegration test results for 69.38 wt. % ciprofloxacin HCl,
  11.78 wt. % Polyox® WSR N-60K, 15% microcrystalline cellulose (MCC), 2.14 wt % PVP, 1.7 wt. % magnesium stearate.
  Tablet dimensions of 10.03×5.76×6.06 mm, tablet weight of 800 mg (containing 555 mg ciprofloxacin HCl), N=6.
Circles, solid line: Dissolution test results for 61.35 wt. % ciprofloxacin HCl,
  14.78 wt. % Polyox® WSR N-60K, 21.87 wt. % Polyox® WSR N-80, 2.0 wt. % stearic acid.
  Tablet dimensions of 8.75×6.45×19.01 mm, tablet weight of 901 mg (containing 553 mg ciprofloxacin HCl), N=3.
Circles, dashed line: Disintegration test results for 61.35 wt % ciprofloxacin
  HCl, 14.78 wt. % Polyox® WSR N-60K, 21.87 wt. % Polyox® WSR N-80, 2.0 wt. % stearic acid.
  Tablet dimensions of 8.75×6.45×19.01 mm, tablet weight of 901 mg (containing 553 mg ciprofloxacin HCl), N=3.
X's, solid line: Dissolution test results for 60.82 wt. % ciprofloxacin
  9 wt. % Polyox® 301, 25.65 wt. % Polyox® WSR N-80, 2.53 wt. % PVP, 2.0 wt. % magnesium stearate.
  Tablet dimensions of 12.04×6.24×19.06 mm, tablet weight of 909 mg (containing 553 mg ciprofloxacin HCl), N=3.
X's, dashed line: Disintegration test results for 60.82 wt. % ciprofloxacin
  9 wt. % Polyox® 301, 25.65 wt. % Polyox® WSR N-80, 2.53 wt. % PVP, 2.0 wt. % magnesium stearate.
  Tablet dimensions of 12.04×6.24×19.06 mm, tablet weight of 909 mg (containing 553 mg ciprofloxacin HCl), N=3.

The formulation containing 13.86% Polyox® N-60K showed a 3-4 hour disintegration profile and approximately 9-hour dissolution profile. When the tablet size was increased to 900-mg and the ratio of drug to Polyox® N-60K was kept constant (using MCC as filler), the increase in tablet size resulted in a slower release rate, both for disintegration (approximately 5 hours) and dissolution (76% at 8 hours). The formulation containing 9% Polyox® 301/25.65% Polyox® N-80 showed a faster disintegration release of 2-3 hours and a dissolution release profile of approximately 8 hours. The presence of Polyox® N-80 appeared to act as an effective tablet disintegrant, while the Polyox® 301 provided tablet integrity. Also, while the Polyox® 301 prevented the tablet from disintegrating too quickly, the Polyox® N-80 allowed for a diffusional release from the tablet matrix.

Figure 6:
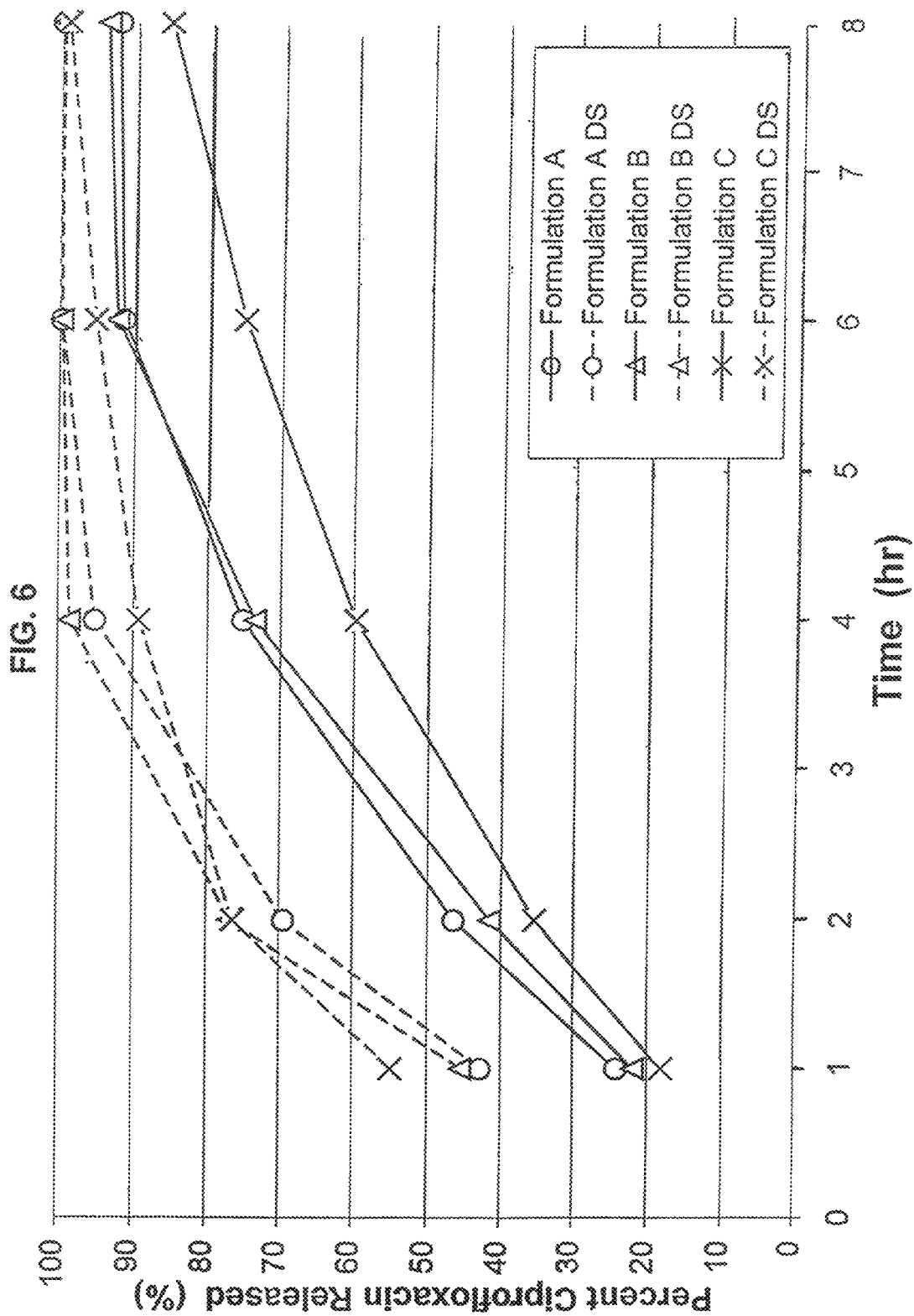
FIG. 6 is a plot showing the release curves obtained from bilayer and trilayer tablets as described in Example 2.

FIG. 6 summarizes the data obtained with bi-layer and tri-layer ciprofloxacin HCl tablets. The bi-layer tablets contained an active layer and a 300-mg swelling layer (Polyox® 303). The tri-layer tablets contained active layers on the top and bottom with a 300-mg Polyox® 303 layer in the middle. The evaluation procedures were the same as those described above, and the formulations together with the symbols used in FIG. 6 where the results are plotted, were as follows:

Circles, solid line: Dissolution test results for bilayer tablet, with layer 1 containing
  60.67 wt. % ciprofloxacin HCl, 34.8 wt. % Polyox® WSR N-80, 2.53 wt. % PVP, 2.0 wt. % magnesium stearate, and layer 2 containing 300 mg Polyox® 303.
  Tablet weight of 1213 mg (containing 554 mg ciprofloxacin HCl), tablet dimensions of 12.02×7.85×19.03 mm, N=3.
Circles, dashed line: Disintegration test results for bilayer tablet, with layer 1 containing
  60.67 wt. % ciprofloxacin HCl, 34.8 wt. % Polyox® WSR N-80, 2.53 wt. % PVP, 2.0 wt. % magnesium stearate, and layer 2 containing 300 mg Polyox® 303.
  Tablet weight of 1213 mg (containing 554 mg ciprofloxacin HCl), tablet dimensions of 12.02×7.85×19.03 mm, N=3.

Triangle, solid line: Dissolution test results for bilayer tablet, with layer 1 containing
- 60.67 wt. % ciprofloxacin 25 wt. % Polyox® WSR N-80, 9.8 wt. % Avicel® PH-101 (MCC), 2.53 wt. % PVP, 2.0 wt. % magnesium stearate, and layer 2 containing
- 300 mg Polyox®303.

Tablet weight of 1217 mg (containing 556 mg ciprofloxacin HCl), tablet dimensions of 12.03×7.79×19.05 mm, N=3.

Triangle, dashed line: Disintegration test results for bilayer tablet, with layer 1 containing
- 60.67 wt. % ciprofloxacin HCl, 25 wt. % Polyox® WSR N-80, 9.8 wt. % Avicel® PH-101 (MCC), 2.53 wt. % PVP, 2.0 wt. % magnesium stearate, and layer 2 containing
- 300 mg Polyox® 303.

Tablet weight of 1217 mg (containing 556 mg ciprofloxacin HCl), tablet dimensions of 12.03×7.79×19.05 mm, N=3.

X's, solid line: Dissolution test results for trilayer tablet, with outer layers each containing
- 46.08 wt. % ciprofloxacin HCl, 10 wt. % Polyox® 301, 40 wt. % Polyox® WSR N-80, 1.92 wt. % PVP, and 2.0 wt. % magnesium stearate, and middle layer containing
- 300 mg Polyox® 303.

Tablet dimensions of 12.00×6.36×19.03 mm, tablet weight of 901 mg (554 mg ciprofloxacin HCl), N=3.

X's, dashed line: Disintegration test results liar trilayer tablet, with outer layers each containing
- 46.08 wt. % ciprofloxacin MC1, 10 wt. % Polyox® 301, 40 wt. % Polyox® WSR N-80, 1.92 wt. % PVP, and 2.0 wt. % magnesium stearate, and middle layer containing
- 300 mg Polyox® 303.

Tablet dimensions of 12.00×6.36×19.03 mm, tablet weight of 901 mg (containing 554 mg ciprofloxacin HCl), N=3.

Example 3

Two formulations (500 mg) of gastric retentive tablets of ciprofloxacin hydrochloride were fabricated under GMP conditions at MDS Pharma Services (Tampa, Fla.). To ensure that ciprofloxacin would not be delivered to the colon, the period of 90% drug release in USP Type I dissolution testing (0.1 N HCl, 100 rpm, pH=1) was designed to be approximately 6 hours. Since retention and drug release represent a balance between swelling and erosion, respectively, 2 formulations were selected. One formulation involved conventional tableting (GR-A) and the other swelled to a greater extent to ensure retention, but was more difficult to manufacture (GR-B). Immediate release tablets (500 mg, Cipro®, Bayer) were used as obtained. The compositions of GR-A and GR-B are given below.

GR-A: 74.26 wt. % ciprofloxacin HCl, 20 wt. % Polyox® 1105, 4.74 wt. % PVP.
1.0 wt. % magnesium stearate. Tablet dimensions of 10.1×6.5×18.1 mm, tablet weight of 796 mg (containing 508 mg ciprofloxacin).

GR-B: Layer 1: 59.41 wt % ciprofloxacin HCl, 35.8 wt. % Polyox® WSR N-80, 3.79 wt. % PVP, 0.99 wt. % magnesium stearate.

Layer 2: 300 mg Polyox® 303.
Tablet dimensions of 12.05×7.9×19.05 mm, tablet weight of 1280 mg (containing 500 mg ciprofloxacin).

Immediate Release (IR) Formulation (caplet, 8.75×6.35×19.09 mm):
500 mg ciprofloxacin tablet (Cipro®, obtained from Bayer Corporation)

The dissolution and disintegration profiles obtained in vitro as described in Example 1 are plotted in FIG. 7. The procedure was repeated using a bicarbonate buffered media (pH=6.8) instead of the 0.1 N HCl solution, and the results are plotted in FIG. 8. The procedure was substantially repeated using mammalian simulated intestinal fluid (mSIF) instead of the 0.1 N HCl solution, and Table 4 shows the percent of ciprofloxacin release from the GR-A formulation at 1 and 6 hours. The GR-A formulation represented a 6-hour system with over 90% drug release in 0.1 HCl.

TABLE 4

Dissolution of Ciprofloxacin GR-A Tablets

| Receptor Media | Percent Released (%) | |
|---|---|---|
| | 1 hour | 6 hour |
| 0.1N HCl | 15.2 | 91.6 |
| mSIF | 0.9 | 3.1 |
| Bicarbonate Buffer | 0.5 | 3.4 |

An analytical test was performed on the solubility of ciprofloxacin in three different solutions, deionized water (DI), mSIF, and a bicarbonate-buffered solution. Ciprofloxacin was added to each solvent gradually until the solution became saturated. Each mixture was then centrifuged and the concentration of ciprofloxacin in the supernatant was analyzed by high performance liquid chromatography. The results are provided in Table 5.

TABLE 5

Solubility of Ciprofloxacin Hydrochloride

| Receptor Media | pH Before adding Ciprofloxacin HCl | pH After Adding Ciprofloxacin HCl | Solubility of Ciprofloxacin HCl (mg/mL) |
|---|---|---|---|
| 0.1N HCl | 5.8 | 3.8 | 30 |
| mSIF | 6.8 | 6.7 | 0.1 |
| Bicarbonate Buffer | 6.8 | 8.2 | 0.1 |

Ciprofloxacin was found to be very insoluble in both mSIF and bicarbonate-buffered solution (pH=6.8).

Example 4

The pharmacokinetics of two formulations of gastric retentive tablets of ciprofloxacin hydrochloride and the immediate release tablet (Cipro® 500 mg base) were compared in 15 healthy volunteers. Retention in the stomach in the fed mode was based on polymeric swelling, and drug release was based on polymeric erosion. Extended release profiles were observed for the gastric retentive tablets with comparable bioavailability to the immediate release tablet.

A single dose, 3-way, open-label, randomized crossover study was conducted under GCP in 15 healthy volunteers at the AAI facility in Neu-Ulm, Germany. All treatments were administered within 5 minutes after a 500-calorie, moderate fat breakfast. There was a 5-day wash out period between treatments. All volunteers were screened and signed informed consent forms prior to enrolling in the study. Plasma samples were taken at 0.5, 1, 1.5, 2, 3, 4, 5, 6, 5, 10, 12, 14, 16, 20, and 24 hours after dosing. Urine was collected for 36 hours. Ciprofloxacin was analyzed in plasma and urine by HPLC. Noncompartmental parameters were calculated for the plasma data. Statistical differences were detected by ANOVA ($p<0.05$).

The mean±S.D. for the pharmacokinetic parameters for each treatment is reported in Table 6. There were no statistical differences in AUC among treatments. The mean bioavailabilities of the two gastric retentive tablets were approximately 90% relative to the immediate release tablet. Statistical differences were detected in terms of a reduction of $C_{max}$ and a greater $t_{max}$ for the gastric retentive tablets compared to the immediate release tablet. No statistical differences were observed between the 2 gastric retentive tablets. Both gastric retentive tablets yielded extended release plasma profiles without significant loss of bioavailability. Plasma profiles in terms of plasma levels versus time are plotted in FIG. 9. In this study, there was a trend toward less variability with the GR-B tablet, but this difference is well within experimental variation. The intersubject variation in delivery for both gastric retentive tablets was comparable to the variation for the immediate release tablet.

TABLE 6

Noncompartmental PK Parameters for Treatments

| Treatment | AUC (ng-h/ml) | Relative Bioavailability | Cmax (ng/ml) | Tmax (h) |
|---|---|---|---|---|
| IR | 7320 ± 2030 | — | 1780 ± 580 | 1.2 ± 0.7 |
| GR-A | 6420 ± 2340 | 0.88 ± 0.21 | 1090 ± 410*** | 3.6 ± 2.0*** |
| GR-B | 6790 ± 2350 | 0.92 ± 0.17 | 1030 ± 390*** | 3.7 ± 1.5*** |

***$p < 0.001$

All three treatments were well tolerated and the adverse reactions were mild and did not appear drug related. Both gastric retentive tablets provided extended duration of plasma profiles for ciprofloxacin and had comparable bioavailability to the immediate release tablet.

The invention claimed is:

1. An oral dosage form consisting essentially of:
a single unencapsulated tablet comprising a single matrix/active agent layer, wherein the single matrix/active agent layer comprises a dose of a first pharmacologically active agent dispersed in a polymer matrix;
wherein the polymer matrix is comprised of a biocompatible, hydrophilic polyalkylene oxide and a disintegrant wherein the polymer matrix has an erosion rate (ER) to dissolution rate (DR) ratio of about 1.2:1 to 5:1,
wherein the tablet upon imbibition of water swells unrestrained dimensionally to a size effective to promote gastric retention for a time period of about 4 to 9 hours, and
wherein upon oral administration the dosage form maintains its size for the time period before it is diminished by erosion,
wherein the first pharmacologically active agent is selected from the group consisting of gabapentin and a neuroleptic agent and is present in an amount in a range of about 60% to about 80% of the dosage form by volume, and
wherein at least 80 wt. % of the first active agent in the dosage form is released by erosion of the polymer matrix within the time period.

2. The dosage form of claim 1, wherein the polyalkylene oxide comprises one selected from the group consisting of poly(ethylene oxide), polyethylene glycol, poly(ethylene oxide)-poly(propylene oxide) copolymers, and combinations thereof.

3. The dosage form of claim 2, wherein the polyalkylene oxide has a number average molecular weight of about 7 million, about 5 million, about 4 million, about 2 million, about 900,000, or about 200,000.

4. The dosage form of claim 1, wherein the polyalkylene oxide comprises a poly(ethylene oxide).

5. The dosage form of claim 1, wherein the therapeutically effective amount of the first active agent in the dosage form is about 60% of the dosage form by volume.

6. The dosage form of claim 1, wherein the dosage form is characterized by an ER to DR ratio of approximately 1.2:1 to approximately 3:1.

7. The dosage form of claim 1, wherein the dosage form is characterized by an ER to DR ratio of approximately 1.3:1 to approximately 2:1.

8. The dosage form of claim 1, wherein the dosage form is characterized by an ER to DR ratio of approximately 1.5:1 to approximately 2:1.

9. The dosage form of claim 1, wherein the neuroleptic agent is selected from the group consisting of antidepressant drugs, antimanic drugs, antipsychotic agents, and antiparkinsonism drugs.

10. The dosage form of claim 1, wherein the first active agent is gabapentin.

11. The dosage form of claim 1, wherein said active agent possesses an aqueous solubility that decreases with increasing pH.

12. The dosage form of claim 11, wherein following administering of said dosage form and gastric retention thereof, the dosage form passes into the lower gastrointestinal tract, whereby active agent remaining in the dosage form is insoluble and unavailable for absorption.

13. The dosage form of claim 1, wherein the matrix/active agent dosage form further comprises a second pharmacologically active agent.

* * * * *